US009556458B2

(12) United States Patent
Beller et al.

(10) Patent No.: US 9,556,458 B2
(45) Date of Patent: Jan. 31, 2017

(54) BACTERIAL PRODUCTION OF METHYL KETONES

(71) Applicant: THE REGENTS OF THE UNIVERSITY OF CALIFORNIA, Oakland, CA (US)

(72) Inventors: Harry R. Beller, Berkeley, CA (US); Ee-Been Goh, Emeryville, CA (US)

(73) Assignee: The Regents of the University of California, Oakland, CA (US)

( * ) Notice: Subject to any disclaimer, the term of this patent is extended or adjusted under 35 U.S.C. 154(b) by 12 days.

(21) Appl. No.: 14/354,510

(22) PCT Filed: Oct. 26, 2012

(86) PCT No.: PCT/US2012/062285
§ 371 (c)(1),
(2) Date: Apr. 25, 2014

(87) PCT Pub. No.: WO2013/063513
PCT Pub. Date: May 2, 2013

(65) Prior Publication Data
US 2014/0370560 A1 Dec. 18, 2014

Related U.S. Application Data

(60) Provisional application No. 61/552,422, filed on Oct. 27, 2011.

(51) Int. Cl.
C12P 7/26 (2006.01)
C12N 1/20 (2006.01)
C12N 9/16 (2006.01)

(52) U.S. Cl.
CPC . *C12P 7/26* (2013.01); *C12N 1/20* (2013.01); *C12N 9/16* (2013.01); *C12Y 301/02* (2013.01); *Y02P 20/52* (2015.11)

(58) Field of Classification Search
None
See application file for complete search history.

(56) References Cited

U.S. PATENT DOCUMENTS

2010/0221798 A1* 9/2010 Schirmer ............... C10L 1/02
435/147
2010/0274033 A1 10/2010 Sanchez-Riera et al.
(Continued)

FOREIGN PATENT DOCUMENTS

WO 00/75350 A2 12/2000
WO 2007/130518 A2 11/2007
(Continued)

OTHER PUBLICATIONS

Patel et al., "Microbial oxidation of gaseous hydrocarbons: Production of methylketones from corresponding n-alkanes by methane-utilizing bacteria", Applied and Environmental Microbiology, vol. 39, No. 4, pp. 727-733, 1980.*
(Continued)

Primary Examiner — Robert Mondesi
Assistant Examiner — Richard Ekstrom
(74) Attorney, Agent, or Firm — Kilpatrick Townsend & Stockton LLP

(57) ABSTRACT

The present invention relates to methods and compositions for increasing production of methyl ketones in a genetically modified host cell that overproduces β-ketoacyl-CoAs through a re-engineered β-oxidation pathway and overexpresses FadM.

17 Claims, 7 Drawing Sheets

(56) References Cited

U.S. PATENT DOCUMENTS

| | | | |
|---|---|---|---|
| 2011/0165637 A1* | 7/2011 | Pfleger | C12N 9/16 |
| | | | 435/134 |
| 2011/0289632 A1* | 11/2011 | Pichersky | C12N 9/16 |
| | | | 800/298 |
| 2015/0184133 A1* | 7/2015 | Beller | C12N 9/001 |
| | | | 435/134 |

FOREIGN PATENT DOCUMENTS

| WO | 2009/140695 A1 | 11/2009 |
|---|---|---|
| WO | 2011/038244 A2 | 3/2011 |

OTHER PUBLICATIONS

GenBank Accession No. EDX43939.1, published Jul. 25, 2008.*
UniProt Accession No. C5CBS9_MICLC, published Jul. 28, 2009.*
UniProt Accession No. FADM_ECOLI, published Feb. 1, 1997.*
Extended European Search Report dated Mar. 2, 2015 for EP Application No. 12842733.3, 12 pages.
Dellomonaco et al., "Engineered reversal of the β-oxidation cycle for the synthesis of fuels and chemicals", *Nature*, vol. 355, pp. 355-361 (2011), with 14 pages of supplementary information.
Engelvin et al., "Identification of β-oxidation and thioesterase activities in *Staphylococcus carnosus* 833 strain", *FEMS Microbiology Letters*, vol. 190, pp. 115-120 (2000).
Goh et al., "Engineering of Bacterial Methyl Ketone Synthesis for Biofuels", *Applied and Environmental Microbiology*, vol. 78, No. 1, pp. 70-80 (2012).
Goh et al., "Substantial improvements in methyl ketone production in *E. coli* and insights on the pathway from in vitro studies", *Metabolic Engineering*, vol. 26, pp. 67-76 (2014).
Janssen et al., "Fatty acid synthesis in *Escherichia coli* and its applications toward the production of fatty acid based biofuels", *Biotechnology for Biofuels*, vol. 7, No. 1, 7 pages (2014).
Park et al., "Synthesis of methyl ketones by metabolically engineered *Escherichia coli*", *J Ind Microbiol Biotechnol*, vol. 3, pp. 1703-1712 (2012).
Yu et al., "Enzymatic Functions of Wild Tomato Methylketone Synthases 1 and 2", *Plant Physiology*, vol. 154, pp. 67-77 (2010).
International Search Report and Written Opinion dated Oct. Feb. 11, 2013 for International Patent Application No. PCT/US2012/062285, 10 pages.
Dellomonaco et al., "Engineered reversal of the β-oxidation cycle for the synthesis of fuels and chemicals", *Nature*, vol. 355, pp. 355-361 (2011).

* cited by examiner

[a] Threshold (Δ) is defined as the difference between the observed and expected score.

[b] FDR = False Discovery Rate

BACTERIAL PRODUCTION OF METHYL KETONES

CROSS-REFERENCE TO RELATED APPLICATIONS

This application is a U.S. National Phase of PCT/US2012/062285, filed Oct. 26, 2012, which claims the benefit of U.S. provisional application No. 61/552,422, filed Oct. 27, 2011, each of which is herein incorporated by reference for all purposes.

STATEMENT AS TO RIGHTS TO INVENTIONS MADE UNDER FEDERALLY SPONSORED RESEARCH AND DEVELOPMENT

The invention described and claimed herein was made utilizing funds supplied by the U.S. Department of Energy under Contract No. DE-AC02-05CH11231. The government has certain rights in this invention.

REFERENCE TO A "SEQUENCE LISTING" SUBMITTED AS AN ASCII TEXT FILE

The Sequence Listing written in file-100-1.TXT, created on Jul. 29, 2014, 28,672 bytes, machine format IBM-PC, MS-Windows operating system, is hereby incorporated by reference in its entirety for all purposes.

BACKGROUND OF THE INVENTION

Aliphatic methyl ketones are naturally occurring compounds that were first discovered in rue (*Ruta graveolens*) more than a century ago (30) and have since been commonly found in microorganisms, plants, insects, and mammalian cells (10). These compounds have a variety of important natural and commercial roles, including acting as pheromones and natural insecticides in plants (1), or providing scents in essential oils and flavoring in cheese and other diary products (10). Biosynthesis of methyl ketones has been hypothesized to derive from a variety of different biological pathways such as fatty acid β-oxidation or aerobic alkene/alkane degradation (10, 21). However, studies to elucidate the genes and biochemical pathways involved in the synthesis of these compounds have been quite rare until recently. One research group in particular has carried out extensive biochemical and genetic studies in a wild tomato species (*Solanum habrochaites*) and identified two key genes, methyl ketone synthase I (ShMKS1) and methyl ketone synthase II (ShMKS2), that are essential for methyl ketone synthesis from fatty acid intermediates in this plant (6, 11, 31). ShMKS2, which belongs to the 4-hydroxybenzoyl-CoA thioesterase (4-HBT) family, is hypothesized to hydrolyze a β-ketoacyl-acyl carrier protein (ACP) thioester intermediate to generate a β-keto acid; ShMKS1, an enzyme that belongs to the α/β-hydrolase superfamily, apparently decarboxylates the β-keto acid released by ShMKS2 to yield a methyl ketone (31).

Despite the commercial relevance of methyl ketones and their prevalence in nature, no genes other than ShMKS1, ShMKS2, and At1g68260 (a ShMKS2 homolog from *Arabidopsis thaliana*), have been recombinantly expressed and shown to be associated with methyl ketone biosynthesis (31). Metabolic engineering of microbes to overproduce methyl ketones merits additional attention, as these compounds could be relevant to the biofuel industry as well as the flavor and fragrance industry by virtue of their highly reduced, aliphatic character. Indeed, a range of other fatty-acid derived compounds have already been successfully synthesized from metabolically engineered microbes for use as biofuels, such as fatty acid ethyl esters (26), alkanes (24), alkenes (5, 18, 22, 28), and n-alcohols (9).

BRIEF SUMMARY OF THE INVENTION

This invention relates, in part, to engineering bacterial host cells, e.g., *E. coli* host cells, to overproduce saturated and monounsaturated methyl ketones for potential application to biofuel production and for use in the flavor and aroma industries. Such engineered host cells overexpress the thioesterase FadM or a variant or homolog thereof and are engineered to modify β-oxidation pathways. The invention thus provides nucleic acid constructs, genetically modified bacterial host cells, methods employing such constructs and host cells to increase the production of methyl ketones.

Thus, in some aspects, the invention provides a genetically modified host cell that produces methyl ketones, wherein the genetically modified is a bacterial host cell transformed with a nucleic acid construct encoding a FadM enzyme that is capable of converting β-ketoacyl-CoA to a β-keto acid, wherein the genetically modified host overproduces β-ketoacyl-CoA. In some embodiments, the genetically modified host cell comprises a nucleic acid that encodes an acyl-CoA oxidase capable of converting an acyl-CoA to a trans-2-enoyl-CoA; and does not express FadA. In some embodiments, the genetically modified host cell further comprises a nucleic acid that encodes a FadB capable of converting trans-2-enoyl-CoA to β-hydroxyacyl-CoA. In some embodiments, genetically modified host cell does not express FadE and comprises a nucleic acid encoding a cytoplasmically-directed (the leader peptide has been removed so the normally periplasmic protein is now cytoplasmic) thioesterase 'tesA gene. In some embodiments, the FadM has at least 50% amino acid sequence identity, or at least 60% amino acid sequence identity, or at least 70%4, at least 75%, at least 80%, at least 85%, at least 90%, or at least 95%, or greater, sequence identity to SEQ ID NO:1. In some embodiments, the FadM is an *E. coli* FadM. In some embodiments the acyl-CoA oxidase has at least 60% amino acid sequence identity, or at least 70%, at least 75%, at least 80%, at least 85%, at least 90%, or at least 95% to SEQ ID NO:2. In some embodiments, the acyl-CoA oxidase is from *Micrococcus luteus*. In some embodiments, the host cell does not express poxB. In some embodiments, the host cell is engineered to overexpress fadR and fadD, e.g. by using a $P_{BAD}$ promoter.

The genetically modified host cell can be any prokaryotic host cell. In some embodiments, the host cell is a bacterial cell selected from the *Escherichia, Enterobacter, Azotobacter, Erwinia, Bacillus, Pseudomonas, Klebsielia, Proteus, Salmonella, Serratia, Shigella, Rhizobia, Ralstonia*, or *Vitreoscilla* taxonomical class. In some embodiments, the prokaryotic cell is an *Escherichia coli* cell.

In a further aspect, the invention provides a method of enhancing production of methyl ketones, the method comprising culturing the genetically modified host cell, e.g., a bacterial host cell, modified as described herein under conditions such that the culturing results in the production of methyl ketones. In some embodiments, the method further comprises isolation of the methyl ketones. In some embodiments, the methyl ketones are isolated using a decane overlay. In some embodiments, the genetically modified host cells that produce methyl ketones as described herein may produce high titers, e.g., titers of more than 800 mg/L (in shake flasks with defined medium containing 1% glucose).

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION OF THE INVENTION

Figure 1:
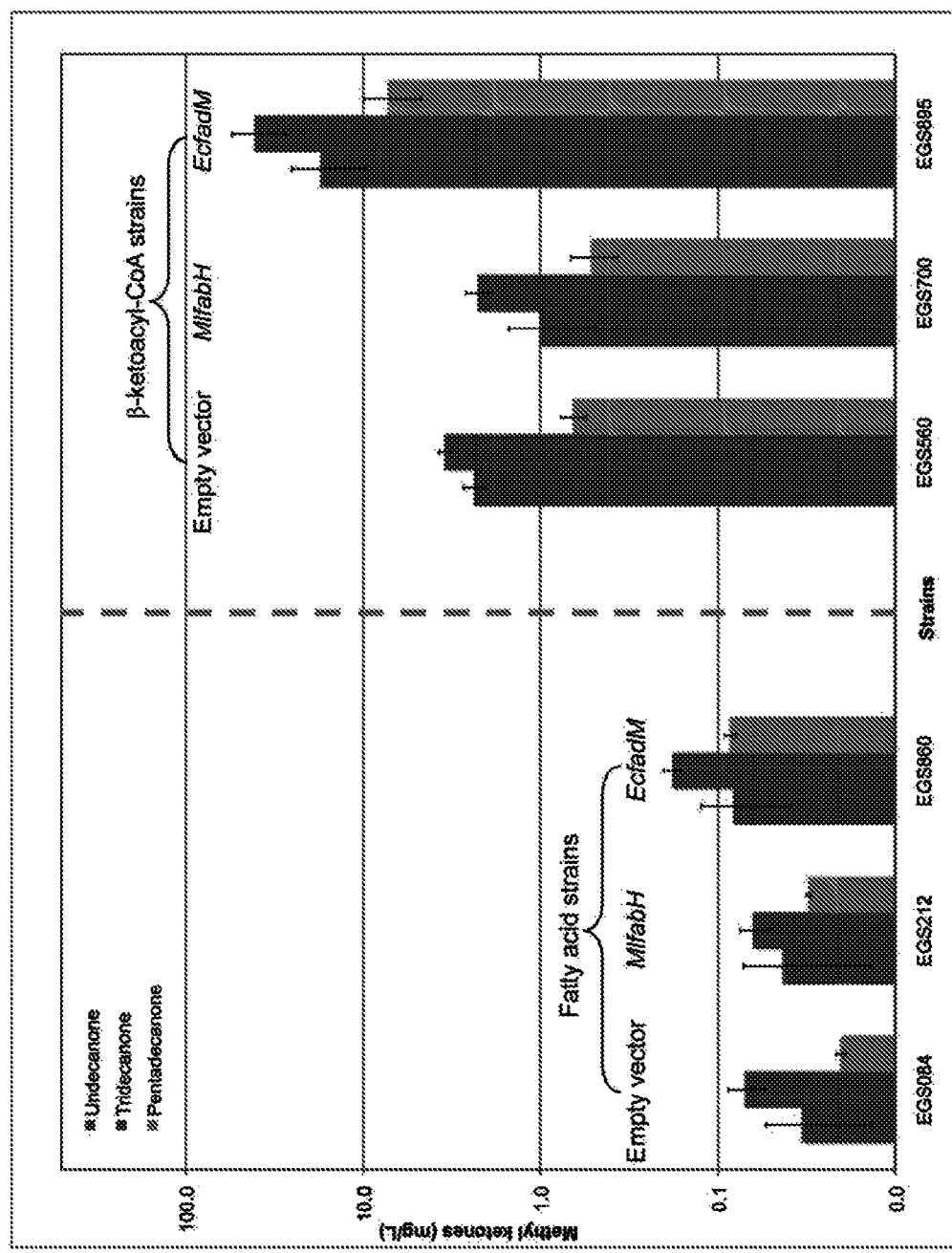
FIG. 1. Methyl ketone production in fatty acid- and β-ketoacyl-CoA-overproducing strains. Bar heights represent the averages of at least three biological replicates and error bars represent one standard deviation.

Before the invention is described in detail, it is to be understood that, unless otherwise indicated, this invention is not limited to particular sequences, expression vectors, enzymes, host microorganisms, or processes, as such may vary. It is also to be understood that the terminology used herein is for purposes of describing particular embodiments only, and is not intended to be limiting.

In order to more fully appreciate the invention the following definitions are provided.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "host cell" and "host microorganism" are used interchangeably herein to refer to a living biological cell that can be transformed via insertion of an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

The term "heterologous DNA" as used herein refers to a polymer of nucleic acids wherein at least one of the following is true: (a) the sequence of nucleic acids is foreign to (i.e., not naturally found in) a given host microorganism; (b) the sequence may be naturally found in a given host microorganism, but in an unnatural (e.g., greater than expected) amount; or (c) the sequence of nucleic acids comprises two or more subsequences that are not found in the same relationship to each other in nature. For example, regarding instance (c), a heterologous nucleic acid sequence that is recombinantly produced will have two or more sequences from unrelated genes arranged to make a new functional nucleic acid. Specifically, the present invention describes the introduction of an expression vector into a host microorganism, wherein the expression vector contains a nucleic acid sequence coding for an enzyme that is not normally found in a host microorganism. With reference to the host microorganism's genome, then, the nucleic acid sequence that codes for the enzyme is heterologous.

The term "FadM" or "FADM" as used herein refers to a thioesterase that converts β-ketoacyl-CoA to a β-keto acid. Standard methods are used to assess whether a polypeptide has FadM activity by measuring the ability of the polypeptide to convert β-ketoacyl-CoA to a β-keto acid, e.g., in cells. Examples of FadM polypeptides and nucleic acids are provided in the tables. As understood in the art, FadM activity need not be assessed directly, but can be assessed by measuring the ability of a FadM variant or homolog to substitute for FadM, e.g., in a bacterial system that produces methyl ketones based on FadM overexpression. Thus, measurement of an endpoint downstream in the reaction pathway can serve as a measure of FadM activity.

As used herein, the term "acyl-CoA oxidase" refers to an enzyme that converts an acyl-CoA to a trans-2-enoyl-CoA. Standard methods such as those described herein and in the examples are used to assess whether a polypeptide has acyl-CoA oxidase activity by measuring the ability of the polypeptide to convert an acyl-CoA to a trans-2-enoyl-CoA, e.g., in cells. Examples of acyl-CoA oxidase polypeptides and nucleic acids suitable for use in the invention are provided in the tables. As understood in the art, acyl-CoA oxidase activity need not be assessed directly, but can be assessed by measuring the ability of an acyl-CoA oxidase variant or homolog to substitute for acyl-CoA oxidase, e.g., in a bacterial system in which acyl-CoA oxidase is overexpressed to produce methyl ketones based on FadM overexpression. Thus, measurement of an endpoint downstream in the reaction pathway can serve as a measure of acyl-CoA oxidase activity.

As used herein, a genetically modified host cell that overproduces β-ketoacyl-CoA is a host cell in which components of the β-oxidation pathway have been modified to overproduce β-ketoacyl-CoA in comparison to a host cell having an unmodified β-oxidation pathway. These modifications typically include overexpression of acyl-CoA oxidase, overexpression of FadB, and inhibition of expression of FadA, e.g., by chromosomal deletion. In some embodiments, FadE expression may also be inhibited, e.g., by chromosomal deletion. In some embodiments, the host cell may comprises further modifications, e.g., expression of a cytosolically-directed thioesterase, e.g., 'TesA.

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Preferred expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

The term "operably linked" refers to a functional linkage between a nucleic acid expression control sequence (such as a promoter) and a second nucleic acid sequence, wherein the expression control sequence directs transcription of the nucleic acid corresponding to the second sequence.

The term "transduce" as used herein refers to the transfer of a sequence of nucleic acids into a host microorganism or cell. Only when the sequence of nucleic acids becomes stably replicated by the cell does the host microorganism or cell become "transformed." As will be appreciated by those of ordinary skill in the art, "transformation" may take place either by incorporation of the sequence of nucleic acids into the cellular genome, i.e., chromosomal integration, or by extrachromosomal integration. In contrast, an expression vector, e.g., a virus, is "infective" when it transduces a host microorganism, replicates, and (without the benefit of any complementary virus or vector) spreads progeny expression vectors, e.g., viruses, of the same type as the original transducing expression vector to other microorganisms, wherein the progeny expression vectors possess the same ability to reproduce.

The terms "isolated" or "biologically pure" refer to material that is substantially or essentially free of components that normally accompany it in its native state.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing normucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochem.* 9:4022, 1970).

The term "functional variant" describes an enzyme that has a polypeptide sequence that is at least 40% or at least 50%, typically at least 55%, at least 60%, at least 65%, at least 70%, at least 75%, at least 80%, at least 85%, at least 90%, at least 95% or at least 99% identical to any one of the enzymes described herein. The "functional variant" enzyme may retain amino acids residues that are recognized as conserved for the enzyme, and may have non-conserved amino acid residues substituted or found to be of a different amino acid, or amino acid(s) inserted or deleted, but which does not affect or has insignificant effect its enzymatic activity as compared to the enzyme described herein. The "functional variant" enzyme has an enzymatic activity that is identical or essentially identical to the enzymatic activity of the enzyme described herein. The "functional variant" enzyme may be found in nature or be an engineered mutant thereof.

"Conservatively modified variants" applies to both amino acid and nucleic acid sequences. With respect to particular nucleic acid sequences, "conservatively modified variants" refers to those nucleic acids that encode identical or essentially identical amino acid sequences, or where the nucleic acid does not encode an amino acid sequence, to essentially identical sequences. Because of the degeneracy of the genetic code, a large number of functionally identical nucleic acids encode any given protein.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. For example, the following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L). Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (e.g., 60% identity, optionally 65%, 70%, 75%, 80%, 85%, 90%, 91%, 92%, 93%, 94%, 95%, 96%, 97%, 98%, or 99% identity over a specified region), when compared and aligned for maximum correspondence over a comparison window, or designated region, or over the full length of the nucleic acid or polypeptide sequence, as measured using one of the following sequence comparison algorithms or by manual alignment and visual inspection. Such sequences are then said to be "substantially identical." This definition also refers to the complement of a test nucleic acid sequence. Optionally, for amino acid sequences, the identity exists over a region that is at least about 50 amino acids in length, or more preferably over a region that is 100 to 500 or 700 or more amino acids in length.

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

These and other objects, advantages, and features of the invention will become apparent to those persons skilled in the art upon reading the details of the invention as more fully described below.

Introduction

In certain aspect, the present invention provides methods and compositions for increasing production of methyl ketones in a genetically modified bacterial host cell where the method comprises overexpressing a fadM gene in a host cell that is modified to overproduce β-ketoacyl-CoA. The invention thus provides genetically modified cells that have been modified to be capable of expression a FadM enzyme encoded by a gene introduced into the host cell.

The fadM gene is overexpressed in a host cell that has been engineered to overproduce β-ketoacyl-CoAs by modifying the fatty acid β-oxidation pathway. Typically, such modified host cells include modifications to overexpress an acyl-CoA oxidase and FadB, and are additionally modified such that FadA expression is inhibited, e.g., by chromosomal deletion. The acyl-CoA oxidase is a soluble protein that replaces FadE. FadA expression is inhibited, typically by deletion to truncate the β-oxidation cycle at β-ketoacyl-CoA. In some embodiments, FadE expression may also be inhibited, e.g., by chromosomal deletion. In some embodiments, the host cell may comprises additional modifications, e.g., expression of a cytosolically-directed thioesterase, e.g., 'TesA, that can enhance fatty acid production.

The invention employs routine techniques in the field of recombinant nucleic acid technology. Basic texts disclosing the general methods of use in this invention include Sambrook & Russell, Molecular Cloning, A Laboratory Manual (3rd Ed, 2001); Kriegler, Gene Transfer and Expression: A Laboratory Manual (1990); and Current Protocols in Molecular Biology (Ausubel et al., eds., 1994-2009, Wiley Interscience).

Enzymes Involved in Methyl Ketone Production

FadM

FadM, or homologous enzyme thereof, is a thioesterase that can catalyze the conversion of β-ketoacyl-CoA to a β-keto acid. FadM is typically characterized in the art as being involved in the β-oxidation of oleic acid. A homologous enzyme is an enzyme that in some embodiments, has a polypeptide sequence that is at least 70%, at least 75%, at least 80%, at least 85%, at least 90%, at least 95% or at least 99% identical to any one of the FadM enzymes described in this specification, e.g., those having an accession number listed in the tables, or in an incorporated reference. The homologous enzyme retains amino acids residues that are recognized as conserved for the enzyme and that are necessary for activity. The homologous enzyme may have non-conserved amino acid residues replaced or found to be of a different amino acid, or amino acid(s) inserted or deleted, but which does not affect or has insignificant effect on the enzymatic activity of the homologous enzyme. The homologous enzyme has an enzymatic activity that is identical or essentially identical to the enzymatic activity any one of the enzymes described in this specification or in an incorporated reference. The homologous enzyme may be found in nature or be an engineered mutant thereof. Amino acid residues/domains of FadM proteins that are important for function are known in the art. For example, FadM protein structure-function has been well characterized (see, e.g., Cantu et al., Thioesterases: a new perspective based on their primary and tertiary structures. *Protein Science* 19:1281-1295, 2010: FadM is in Family TE5 in this reference).

Example of suitable FadM enzymes include those from *E. coli* as well as FadM enzymes encoded by the genes identified by their accession number in the tables. In some embodiments suitable FadM enzymes are from *Escherichia* sp., *Shigella* sp., *Citrobacter* sp., *Salmonella* sp, *Entero-* bacter sp., *Cronobacter* sp., *Klebsiella* sp, *Serratia* sp., *Yersinia* sp, *Pantoea* sp., *Rahnella* sp., *Yersinia* sp., *Erwinia* sp., or *Pectobacterium* sp.

An exemplar protein sequence is provided in SEQ ID NO:1. In some embodiments, a genetically modified host cell in accordance with the invention has a nucleic acid construct that encodes a FadM that has at least 60%, typically at last 65%, or at least 70%, at least 75%, at least 80%, at least 85%, at least 90%, or least 95% identity to SEQ ID NO:1.

Acyl-CoA Oxidases

An acyl-CoA oxidase useful in the invention catalyzes the conversion of an acyl-CoA to a trans-2-enoyl-CoA. A homologous enzyme is an enzyme that in some embodiments, has a polypeptide sequence that is at least 70%, 75%, 80%, 85%, 90%, 95% or 99% identical to any one of the acyl-CoA oxidase sequences described in this specification, e.g., those having an accession number listed in the tables or in an incorporated reference. The homologous enzyme retains amino acids residues that are recognized as conserved for the enzyme and that are necessary for activity. The homologous enzyme may have non-conserved amino acid residues replaced or found to be of a different amino acid, or amino acid(s) inserted or deleted, but which does not affect or has insignificant effect on the enzymatic activity of the homologous enzyme. The homologous enzyme has an enzymatic activity that is identical or essentially identical to the enzymatic activity any one of the enzymes described in this specification or in an incorporated reference. The homologous enzyme may be found in nature or be an engineered mutant thereof. Amino acid residues/domains of acyl-CoA oxidases that are important for function are known in the art. For example, acyl-CoA oxidase protein structure function has been well characterized (see, e.g., Kim & Miura Acyl-CoA dehydrogenases and acyl-CoA oxidases: structural basis for mechanistic similarities and differences. *Eur J Biochem.* 271: 483-493, 2004).

Example of suitable acyl-CoA oxidase enzymes include those from *Micrococcus luteus*, such as *Micrococcus luteus* NCTC 2665, as well as acyl-CoA oxidase encoded by the genes identified by their accession number in the tables. In some embodiments, suitable acyl-CoA oxidase enzymes are from *Arthrobacter* sp., *Corynebacterium*, marine *Actinobacterium* sp, *Renibacteria*, sp. *Clavibacter* sp. *Lefisonia* sp, *Kocuria* sp., *Cellulomonas* sp., *Cellvibril* sp., and *Isoptericola* sp.

An exemplar acyl-CoA oxidase protein sequence is provided in SEQ ID NO:2 In some embodiments, a genetically modified host cell in accordance with the invention has a nucleic acid construct that encodes an acyl-CoA oxidase that has at least 60%, typically at last 65%, or at least 70%, at least 75%, at least 80%, at least 85%, at least 90%, or least 95% identity to SEQ ID NO:2.

FadB Enzymes

A FadB useful in the invention catalyzes the conversion of a trans-2-enoyl-CoA to a β-hydroxyacyl-CoA and oxidation of a β-hydroxyacyl-CoA to a β-ketoacyl-CoA. A homologous enzyme is an enzyme that in some embodiments, has a polypeptide sequence that is at least 70%, 75%, 80%, 85%, 90%, 95% or 99% identical to any one of the FadB sequences described in this specification, e.g., those having an accession number listed in the tables, or in an incorporated reference. The homologous enzyme retains amino acids residues that are recognized as conserved for the enzyme and that are necessary for activity. The homologous enzyme may have non-conserved amino acid residues replaced or found to be of a different amino acid, or amino acid(s) inserted or deleted, but which does not affect or has insignificant effect on the enzymatic activity of the homologous enzyme. The homologous enzyme has an enzymatic activity that is identical or essentially identical to the enzymatic activity any one of the enzymes described in this specification or in an incorporated reference. The homologous enzyme may be found in nature or be an engineered mutant thereof. Residues/domains important for function are known in the art and can be determined, e.g., by alignment of FadB protein sequences.

Examples of suitable FadB enzymes include those from *E. coli*, such as *E. coli* DH1, as well as FadB enzymes encoded by the genes identified by their accession number in the tables. In some embodiments, suitable FadB enzymes are from *Salmonella* sp. or *Shigella* sp.

An exemplar FadB protein sequence is provided in SEQ ID NO:3 In some embodiments, a genetically modified host cell in accordance with the invention has a nucleic acid construct that encodes a FadB that has at least 60%, typically at last 65%, or at least 70%, at least 75%, at least 80%, at least 85%, at least 90%, or least 95% identity to SEQ ID NO:3.

Other Host Cell Modifications to Overproduce β-Ketoacyl-CoAs

The genetically modified host cells that produce methyl ketones also include additional modifications, such as modification to inhibit expression of FadA. FadA is expressed with FadB as an operon. The fadA gene is downstream of fadB (see, e.g., Yang et al., *J. Biol. Chem.* 265:10424-10429, 1990). Such inhibition of expression is typically achieved by deleting all or a part of the FadA gene. Methods of knocking out bacterial genes are well known in the art (see, e.g., Baba et al, *Mol. Syst. Biol* 2:2006.0008, 2006; Datsenko et al., *Proc. Natl. Acad. Sci. USA* 97:664-6645, 2000).

Optionally, FadE expression may also be inhibited, e.g., by using chromosomal deletion techniques.

In some embodiments, a genetically modified host cell can further comprise a genetic modification whereby the host cell is modified by the increased expression of one or more genes involved in the production of fatty acid compounds. Such genes include a cytosolically directed thioesterase ('TesA) (see, e.g., Steen, et al., *Nature* 463:559-62, 2010).

In some embodiments, a genetically modified host cell may also overexpress FadR. FadR is a dual DNA-binding transcription regulator involved in several processes in the fatty acid pathway, including fatty acid activation, membrane transportation, degradation and conversion to unsaturated fatty acids. FadR controls the expression of several gene involved in fatty acid transport and β-oxidation, e.g. fadBA, fadD, fadL, and fadE. FadR sequences are known and can be overexpressed using known techniques (see, e.g., U.S. patent application Ser. No. 13/549,034, which is incorporated by reference).

Nucleic Acid Constructs

The nucleic acid constructs of the present invention comprise nucleic acid sequences encoding one or more of the subject enzymes. The nucleic acid of the subject enzymes are operably linked to promoters and optionally control sequences such that the subject enzymes are expressed in a host cell cultured under suitable conditions. The promoters and control sequences are specific for each host cell species. In some embodiments, expression vectors comprise the nucleic acid constructs. Methods for designing and making nucleic acid constructs and expression vectors are well known to those skilled in the art.

Fragments of nucleic acids encoding the subject enzymes are prepared by any suitable method known to those of ordinary skill in the art, including, for example, direct chemical synthesis or cloning, e.g., using PCR methodology. The recombinant nucleic acid can encode an open reading frame (ORF) of an enzyme of the present invention, e.g., a FadM enzyme, an acyl-CoA oxidase enzyme, or a FadB enzyme. The recombinant nucleic acid can also comprise promoter sequences for transcribing the ORF in a suitable host cell. The recombinant nucleic acid can also comprise sequences sufficient for having the recombinant nucleic acid stably replicate in a host cell. The recombinant nucleic acid can be replicon capable of stable maintenance in a host cell. In some embodiments, the replicon is stably integrated into a chromosome of the host cell. In some embodiments, the replicon is a plasmid. The present invention also provides for a vector or expression vector comprising a recombinant nucleic acid of the present invention. The present invention provides for a host cell comprising any of the recombinant nucleic acids and/or enzymes of the present invention. In some embodiments, enzymes that are overexpressed may be encoded by nucleic acid constructs present on one plasmid. In other embodiments, the enzymes may be encoded by nucleic acid constructs on separate plasmids. For example, FadB and acyl-CoA oxidase may be encoded by FadB genes and acyl-CoA oxidase genes present in the same plasmid, or alternatively, the genes may be present in separate plasmids.

It will be apparent to one of skill in the art that a variety of recombinant vectors can be utilized in the practice of aspects of the invention. As used herein, "vector" refers to polynucleotide elements that are used to introduce recombinant nucleic acid into cells for either expression or replication. Selection and use of such vehicles is routine in the art. An "expression vector" includes vectors capable of expressing DNAs that are operatively linked with regulatory sequences, such as promoter regions. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those that integrate into the host cell genome.

The vectors may be chosen to contain control sequences operably linked to the resulting coding sequences in a manner that expression of the coding sequences may be effected in an appropriate host. Suitable control sequences include those that function in prokaryotic host cells. If the cloning vectors employed to express genes encoding enzymes involved in methyl ketone-production as described herein lack control sequences for expression operably linked to the encoding nucleotide sequences, the nucleotide sequences are inserted into appropriate expression vectors. This can be done individually, or using a pool of isolated encoding nucleotide sequences, which can be inserted into host vectors, the resulting vectors transformed or transfected into host cells, and the resulting cells plated out into individual colonies. Suitable control sequences for controlling expression of genes of various types of organisms are well known in the art. Control systems for expression in suitable host cells, such as prokaryotic host cells, are widely available and are routinely used. Control elements include promoters, optionally containing operator sequences, and other elements depending on the nature of the host, such as ribosome binding sites. Useful promoters for prokaryotic hosts include those from native genes encoding proteins involved in fatty acid production. Other bacterial promoters useful in the methods of the invention include lac promoters, trp promoters, arabinose promoters, and the β-lactamase (bla), bacteriophage lambda PL, and T5 promoters. In addition, synthetic promoters, such as the tac promoter can be used.

As noted, useful control sequences include those which themselves, or with suitable regulatory systems, activate expression during transition from growth to stationary phase in the vegetative mycelium. Other regulatory sequences may also be desirable which allow for regulation of expression of the genes encoding the enzymes involved in methyl ketone production relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors. A variety of markers are known which are useful in selecting for transformed cell lines and generally comprise a gene whose expression confers a selectable phenotype on transformed cells when the cells are grown in an appropriate selective medium. Such markers include, for example, genes that confer antibiotic resistance or sensitivity to the plasmid.

As noted above, the various genes encoding the enzymes involved in methyl ketone produce as described herein, or a mixture of such genes, can be cloned into one or more recombinant vectors as individual cassettes, with separate control elements or under the control of a single promoter. Methods for introducing the recombinant vectors of the present invention into suitable hosts are known to those of skill in the art and typically include the use of $CaCl_2$-based techniques, electroporation techniques and the like.

Although any suitable expression vector may be used to incorporate the desired sequences, readily available expression vectors include, without limitation: plasmids, such as pSC101, pBR322, pBBR1MCS-3, pUR, pEX, pMR100, pCR4, pBAD24, pUC vectors; bacteriophages, such as M13 phage and λ phage. Of course, such expression vectors may only be suitable for particular host cells. One of ordinary skill in the art, however, can readily determine through routine experimentation whether any particular expression vector is suited for any given host cell. For example, the expression vector can be introduced into the host cell, which is then monitored for viability and expression of the sequences contained in the vector. In addition, reference may be made to the relevant texts and literature, which describe expression vectors and their suitability to any particular host cell.

Once the host cell has been transformed with the expression vector, the host cell is allowed to grow. For microbial hosts, this process entails culturing the cells in a suitable medium under conditions such that the recombinant enzymes are produced and β-ketoacyl-CoAs are produced. It is important that the culture medium contain an excess carbon source, such as a sugar (e.g., glucose) when an intermediate is not introduced. In this way, cellular production of β-ketoacyl-CoAs, the starting material for the production of the methyl ketones, is ensured. When added, the intermediate is present in an excess amount in the culture medium.

As the host cell grows and/or multiplies, expression of the enzymes necessary for producing β-ketoacyl-CoAs and converting them to methyl ketones is effected. Once expressed, the enzymes catalyze the steps necessary for carrying out the enzymatic steps shown in FIG. 2. If an intermediate has been introduced, the expressed enzymes catalyze those steps necessary to convert the intermediate into the respective compound for methyl ketone production.

The present invention provides for methyl ketone compounds produced from the method of the present invention. Isolating the methyl ketones involves the separating at least part or all of the host cells, and parts thereof, from which the methyl ketone compound was produced, from the isolated methyl ketone compound. The isolated methyl ketone may be free or essentially free of impurities formed from at least part or all of the host cells, and parts thereof. The isolated methyl ketone is essentially free of these impurities when the amount and properties of the impurities do not interfere in the use of the methyl ketone for a fuel or in the flavor/aroma industry. These host cells are specifically cells that do not in nature produce the desired methyl ketone compound.

The methyl ketones produced in accordance with the invention may be recovered using known methods. For example, the host cells may be harvested and the methyl ketones extracted from the cell pellet (see, e.g., Beller et al., Appl. Environ. Microbiol. 76:1212-23, 2010). In some embodiments, decane overlays may be employed to extract the methyl ketones. An illustrative decane overlay extraction methodology is provided in the Examples section.

The methyl ketones find use in many applications, e.g., for the production of diesel fuels and in the flavor and aroma industry.

Host Cells

Figure 2:
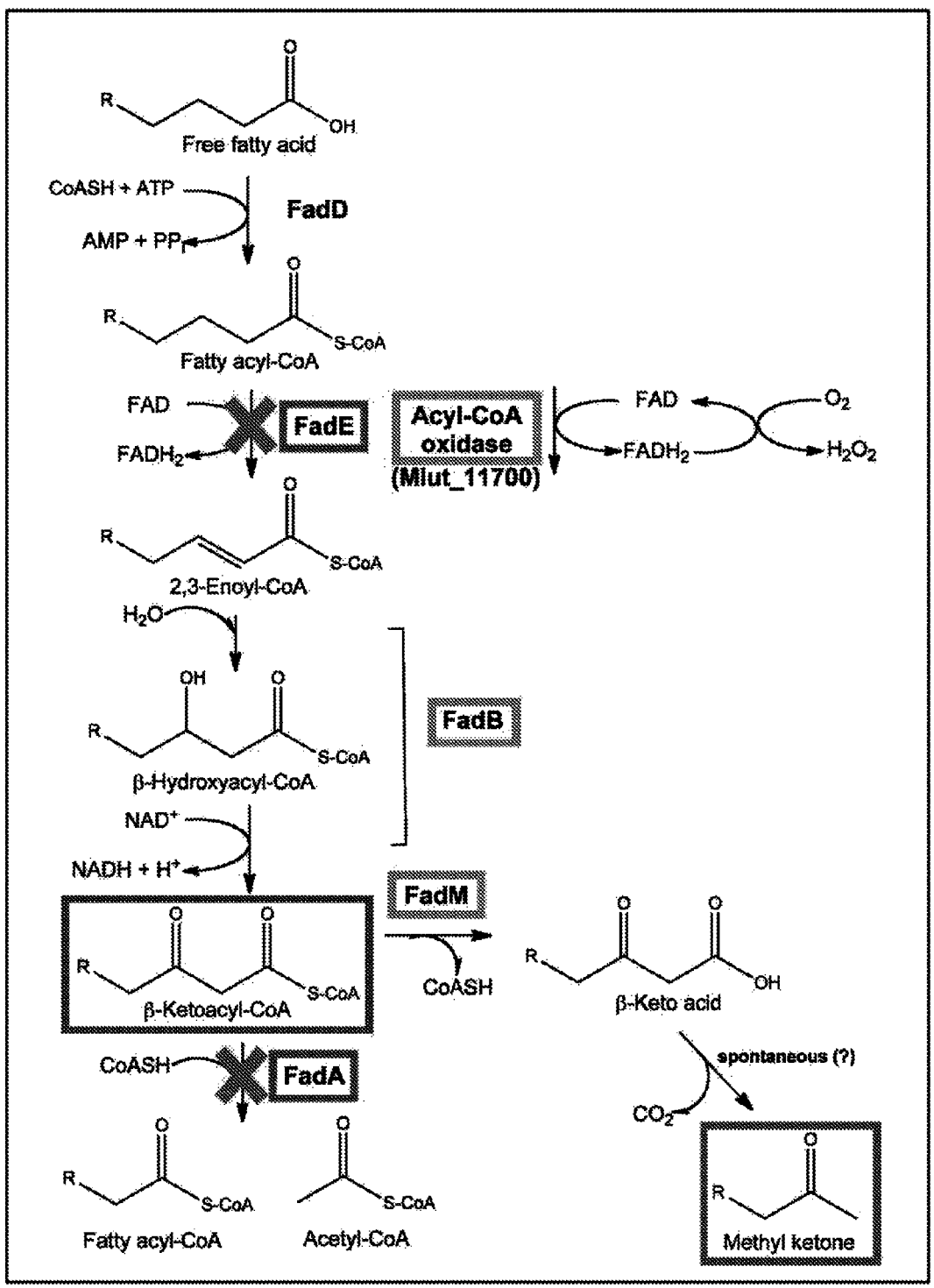
FIG. 2. Summary of engineered pathway to convert fatty acids to methyl ketones in *E. coli* DH1. Green boxes indicate overexpressed genes and red boxes indicate chromosomal deletions. The blue box indicates the putative substrate for FadM (producing free β-keto acids) and the purple box indicates the final methyl ketone product (putatively generated by spontaneous decarboxylation of β-keto acids). The 'TesA thioesterase used for fatty acid overproduction is not depicted in this figure.

The host cells of the present invention are genetically modified in that heterologous nucleic acid have been introduced into the host cells and/or that endogenous gene expression is inhibited, e.g., by chromosomal deletion, and as such the genetically modified host cells do not occur in nature. The suitable host cell is one capable of expressing a nucleic acid construct encoding an enzyme capable of catalyzing a desired biosynthetic reaction in order to produce the enzyme for producing the desired fatty acid molecule. Such enzymes are described herein. In some embodiments, the host cell naturally produces any of the precursors, as shown in FIG. 2, for the production of methyl ketones. These genes encoding the desired enzymes may be heterologous to the host cell or these genes may be native to the host cell but are operatively linked to heterologous promoters and/or control regions which result in the higher expression of the gene(s) in the host cell. In other embodiments, the host cell does not naturally overproduce the fatty acid starting material and comprise heterologous nucleic acid constructs capable of expressing one or more genes necessary for overproducing the fatty acid.

Each of the desired enzyme capable of catalyzing the desired reaction can be native or heterologous to the host cell. Where the enzyme is native to the host cell, the host cell is optionally genetically modified to modulate expression of the enzyme. This modification can involve the modification of the chromosomal gene encoding the enzyme in the host cell or a nucleic acid construct encoding the gene of the enzyme is introduced into the host cell. One of the effects of the modification is the expression of the enzyme is modulated in the host cell, such as the increased expression of the enzyme in the host cell as compared to the expression of the enzyme in an unmodified host cell.

As noted above, the genetically modified host cell can further comprise a genetic modification whereby the host cell is modified by the increased expression of one or more genes involved in the overproduction of fatty acid compounds. Examples of such genes include genes encoding acetyl-CoA carboxylase to increase intracellular malonyl-CoA.

Any prokaryotic host cell may be used in the present method so long as it remains viable after being transformed with a sequence of nucleic acids. Generally, although not necessarily, the host microorganism is bacterial. In some embodiments, the bacteria may be a cyanobacterium. Examples of bacterial host cells include, without limitation, those species assigned to the *Escherichia, Enterobacter, Azotobacter, Erwinia, Bacillus, Pseudomonas, Klebsielia, Proteus, Salmonella, Serratia, Shigella, Ralstonia, Rhizobia, Vitreoscilla, Synechococcus, Synechocystis,* and *Paracoccus* taxonomical classes. Preferably, the host cell is not adversely affected by the transduction of the necessary nucleic acid sequences, the subsequent expression of the enzymes, or the resulting intermediates required for carrying out the steps associated with the methyl ketone production pathway.

In some embodiments, the host cells is *Ralstonia eutropha*. An example of a *R. eutropha* strain is, *R. eutropha* H16, which is engineered to produce fatty acid-derived hydrocarbon biofuels. *R. eutropha* H16 is engineered for production of alkanes through the acyl-ACP reductase/aldehyde decarbonylase pathway from *S. elongates* (see, e.g., Schirmer et al., Microbial Biosynthesis of Alkanes, Science 329:559-562, 2010). *R. eutropha* H16 is additionally described in U.S. provisional patent application 61/557,357, which is incorporated by reference.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

EXAMPLES

Example 1

Expression of Methyl-Ketone-Generating Enzymes in *E. coli*

Materials and Methods

Bacterial strains, plasmids, oligonucleotides, and reagents. Bacterial strains and plasmids used in this study are listed in Table 1. Plasmid extractions were carried out using the QIAGEN (Valencia, Calif.) miniprep and midiprep kits. Oligonucleotide primers were designed using the web-based PrimerBlast program (see, the ncbi www website ncbi.nlm.nih.gov/tools/primer-blast/index.cgi?LINK_LOC=BlastHomeAd) and synthesized by Bioneer (Alameda, Calif.). Primer sequences for amplification of *E. coli* DH1 and *Micrococcus luteus* ORFs are listed in Table 2. The coding sequences (CDS) corresponding to the enzymes ShMKS1 (GenBank accession no. AAV87156) (11) and ShMKS2 (GenBank accession no. ADK38536) (31) from *S. habrochaites*, and UcFatB1 (GenBank accession no. Q41635) from *Umbellularia californica* (32) were synthesized and codon optimized for expression in *E. coli* by GenScript (Piscataway, N.J.). Codon-optimized sequences are listed in Table 8.

Media and Bacterial Growth.

E. coli was propagated as previously described (23). For studies of heterologous gene expression in E. coli strains, cells were grown in 15 ml of tryptic soy broth (containing 0.2% glucose) in 30-ml glass tubes with 200-rpm agitation at 37° C., unless indicated otherwise, for up to 72 hours before being harvested for analysis. Frozen glycerol stocks were used as inocula for the studies described here, unless noted otherwise. When required, antibiotics were added to the growth medium at the following final concentrations: chloramphenicol, 25 µg/ml kanamycin, 50 µg/ml. A final concentration of 0.5 mM IPTG was added to cultures after 6 hours when induction of genes was required.

Plasmid and strain construction for heterologous expression in E. coli. Cloning of M. luteus and E. coli genes into expression plasmids were carried out as previously described (5). All primers used to amplify target genes are listed in Table 2. PCR products and plasmid DNA were digested with the appropriate restriction enzymes and purified with QIAquick gel extraction and/or PCR purification kits (QIAGEN) before being ligated and transformed into E. coli. When no appropriate restriction sites were available for generating cohesive ends for ligation, sequence and ligation independent cloning (SLIC) was performed as described by Li and Elledge (17). Proper clone construction was confirmed by DNA sequencing, which was performed by Quintara Biosciences (Berkeley, Calif.). Expression of heterologous genes in constructs was confirmed by extraction of proteins, tryptic digestion, and analysis of the resulting peptides by electrospray ionization liquid chromatography-tandem mass spectrometry (LC/MS/MS) (QSTAR Elite Hybrid Quadrupole TOF, Applied Biosystems). Mutations of genes were performed as described for the QuikChange site-directed mutagenesis kit (Agilent) using primers designed with nucleotide changes that corresponded to the desired amino acid substitutions. To knock out E. coli genes, in-frame chromosomal deletion of E. coli genes was carried using the method of Datsenko and co-workers (2, 7).

Extraction of methyl ketones and related metabolites from bacterial cultures. For most samples, methyl ketones and other metabolites were extracted from cultures using a decane overlay. For overlay extractions, 1 ml of decane (Sigma, ReagentPlus≥99% purity) amended with perdeuterated decane ($C_{10}D_{22}$) and tetracosane ($C_{24}D_{50}$) internal standards was added to fifteen-ml cultures in 30-ml glass tubes following induction with IPTG. 50 µl of decane overlay was removed at specified time points, up to 72 hrs, for direct gas chromatography-mass spectrometry (GC/MS) analysis. For low-concentration samples in which methyl ketones were not detectable using decane overlays, extractions of cell pellets were performed as previously described (5). For all extractions, culture tubes were pre-cleaned with high purity acetone before being autoclaved. All other glass and PTFE surfaces were also rigorously cleaned with high-purity acetone and an effort was made to ensure that solvent extracts contacted only glass or PTFE surfaces, whenever possible. Metabolite data described in the Results section are from 72-hr overlays unless indicated otherwise. For fatty acid analysis, 50-µl aliquots of extracts were derivatized with ethereal diazomethane to generate fatty acid methyl esters (FAME), as previously described (5).

Analysis by GC/MS.

For electron ionization (EI) GC/MS analyses with a quadrupole mass spectrometer, studies were performed with a model 7890A GC (Agilent) with a DB-5 fused silica capillary column (30-m length, 0.25-mm inner diameter, 0.25-µm film thickness; J & W Scientific) coupled to an HP 5975C series mass selective detector; 1l injections were performed by a model 7683B autosampler. The GC oven was typically programmed from 40° C. (held for 3 min) to 300° C. at 15° C./min and then held for 5 min; the injection port temperature was 250° C., and the transfer line temperature was 280° C. The carrier gas, ultra high-purity helium, flowed at a constant rate of 1 ml/min. Injections were splitless, with the split turned on after 0.5 min. For full-scan data acquisition, the MS typically scanned from 50 to 600 atomic mass units at a rate of 2.7 scans per s. For saturated methyl ketones ($C_{11}$, $C_{13}$, $C_{15}$), external standard quantification (m/z 58 areas) was performed with authentic standards. For monounsaturated ketones, no authentic standards were available, so external standard quantification relied on total ion chromatogram (TIC) areas and saturated methyl ketone standards with the appropriate chain length. Thus, in the absence of authentic standards, unsaturated methyl ketone data should be considered as estimates.

Analysis by liquid chromatography—atmospheric pressure chemical ionization—time of flight (LC-APCI-TOF) mass spectrometry. Liquid chromatographic separation of methyl ketones was conducted at 55° C. with an Inertsil ODS-3 reverse-phase column (250-mm length, 2.1-mm internal diameter, 3-µm particle size; GL Sciences, Inc., Torrance, Calif.) using a 1200 Series HPLC (high-performance liquid chromatography) system (Agilent Technologies, CA). The injection volume for each measurement was 2 µl. The mobile phase was composed of water (solvent A) and methanol (solvent B) (HPLC grade, Honeywell Burdick & Jackson, C A). Methyl ketones were separated with the following gradient: 60% to 98% B for 10 min, held at 98% B for 15 min, 98% to 60% B for 17 min, held at 60% B for 8 min. A flow rate of 0.19 mL/min was used throughout.

The HPLC system was coupled to an Agilent Technologies 6210 time-of-flight mass spectrometer (TOF MS) with a 1:4 post-column split. Nitrogen gas was used as both the nebulizing and drying gas to facilitate the production of gas-phase ions. The drying and nebulizing gases were set to 10 l/min and 30 psi, respectively, and a drying gas temperature of 325° C. was used throughout. The vaporizer and corona were set to 350° C. and 4 µA, respectively. APCI was conducted in the positive-ion mode with a capillary voltage of 3 kV. MS experiments were carried out in the full-scan mode (m/z 102-1000) at 0.86 spectra per s for the detection of [M+H]⁺ ions. The instrument was tuned for a range of m/z 50-1700. Prior to LC-APCI-TOF MS analysis, the TOF MS was calibrated with the Agilent APCI TOF tuning mix. Data acquisition and processing were performed by the MassHunter software package (Agilent Technologies).

In Vitro Assay to Generate Pentadecenone.

His-tagged acyl-CoA oxidase (Mlut_11700) and His-tagged E. coli FadB were purified as previously described (5). A 1-ml acyl-CoA oxidase assay was conducted in a screw-cap glass vial containing 1.5 mM palmitoleoyl-CoA (Sigma), 400 µg of acyl-CoA oxidase, 150 µg/ml BSA, 0.1 mM FAD, and 0.1 M potassium phosphate buffer (pH 7.5). The reaction was incubated on a rotary shaker at 30° C. for 3 hr and 4 U of catalase (Sigma) was added to the mixture and incubated as before for another 30 min at 37° C. to remove the $H_2O_2$ generated by the acyl-CoA oxidase. 250 µl of the acyl-CoA oxidase reaction mixture was added to a 4-ml screw-cap glass vial with a polytetrafluoroethylene (PTFE)-lined septum for the 1-ml FadB assay, which also contained 400 µg/ml of BSA, 300 mM NAD, 600 µg of FadB, and 0.1 M potassium phosphate buffer (pH 7.5). Controls included assay mixtures without FadB. Reactions were incubated on the rotary shaker overnight (~18 hrs) at 37° C. For extraction of assay products, 1 ml hexane (amended with $C_{10}D_{22}$ internal standard) was added to the assay solution, mixed well, allowed to sit for 20 min, and the solvent layer was transferred to a 10-ml conical glass vial. The extraction step was repeated and the two 1-mL aliquots of hexane were combined and then concentrated to 50 µl under a gentle stream of ultra high-purity $N_2$ for subsequent analysis by GC/MS.

Transcriptional studies of E. coli with reverse transcription-quantitative Polymerase Chain Reaction (RT-qPCR) and microarray analyses. For transcriptional studies, E. coli cultures were grown in 15 ml of tryptic soy broth in a 30-ml glass tube as described above, induced with IPTG after 6 hours, and harvested at 8 hours into 2 ml of ethanol solution containing 5% phenol to stop further transcription and preserve RNA integrity. Cell cultures were spun down and the pellets were immediately frozen in liquid nitrogen and stored at −80° C. until RNA extraction. Extraction and purification of RNA were carried out with the QIAGEN RNeasy Mini kit and treated on-column with RNase-free DNase I (Qiagen). Concentration and integrity of RNA were determined with a Thermo Scientific Nanodrop ND-1000 spectrophotometer and an Agilent 2100 BioAnalyzer, respectively.

Synthesis of cDNA for RT-qPCR analysis was carried out using 1 µg of total RNA primed with 60 µM of random hexamers and reverse transcribed using a Transcriptor First Strand cDNA synthesis kit (Roche, Germany). qPCR analyses were then conducted on an Applied Biosystems StepOne system using 1 µl of the reverse transcription reaction and gene-specific primers (Table 2) and the PerfeCTa SYBR Green FastMix (Quanta Biosciences, Gaithersburg, Md.). Quantitative PCR cycle parameters were as follows: initial denaturation at 95° C. for 5 min, followed by 40 cycles of 1 s denaturation at 95° C. and 30 s annealing and extension at 60° C. Fluorescence measurements were taken between each cycle. At the conclusion of the qPCR cycle, melting curve analysis was conducted by denaturing the PCR products from 60° C. to 95° C. and making fluorescence measurements at 0.3° C. increments. All reactions were performed in triplicate. Transcripts were quantified with a standard curve generated by serial dilution of pEG855 (from $10^5$ to $10^{10}$ copies/reaction) and normalized to the internal reference gene, hcaT (34).

To perform microarray analyses, 10 µg of total RNA primed with 5 µg of random hexamers (Roche, Germany) were reverse transcribed using the SuperScript™ Indirect cDNA labeling kit (Invitrogen). Alexa Fluor 555 dyes (Invitrogen) were then incorporated into amino-allyl-dUTP-labeled cDNA, the fluorescently labeled cDNA was purified with the QiaQuick PCR purification kit (Qiagen) and dried under vacuum (Vacufuge Speed Vac, Eppendorf). Labeled cDNA was hybridized to the four-plex NimbleGen E. coli K-12 (Roche) Expression microarray chip (catalog no. A6697-00-01), which contains duplicates of 8 different 60-mer probes for each of the 4,254 genes in the E. coli K-12 genome, at 42° C. for 20-24 hours as recommended by the manufacturer. After hybridization, microarray chips were scanned with a GenePix 4000B scanner and data were extracted using NimbleScan software. Array normalization was performed using the Robust Multiarray Average (RMA) technique as described by Irizarry et al (13). The normalized expression values generated in RMA pair files were imported into Excel and statistical analyses were performed with the Significance Analysis of Microarray (SAM) add-on (29).

Cetane Number Determination.

Cetane number (CN) determinations of selected methyl ketones (Sigma) were performed by the Southwest Research Institute (San Antonio, Tex.) according to ASTM (American Society for Testing and Materials) method D613, with no modifications.

Microarray Data Accession Number.

Microarray data have been deposited in the Gene Expression Omnibus database (http://www.ncbi.nlm.nih.gov/geo) under accession number GPL14649.

Results

Figure 5:
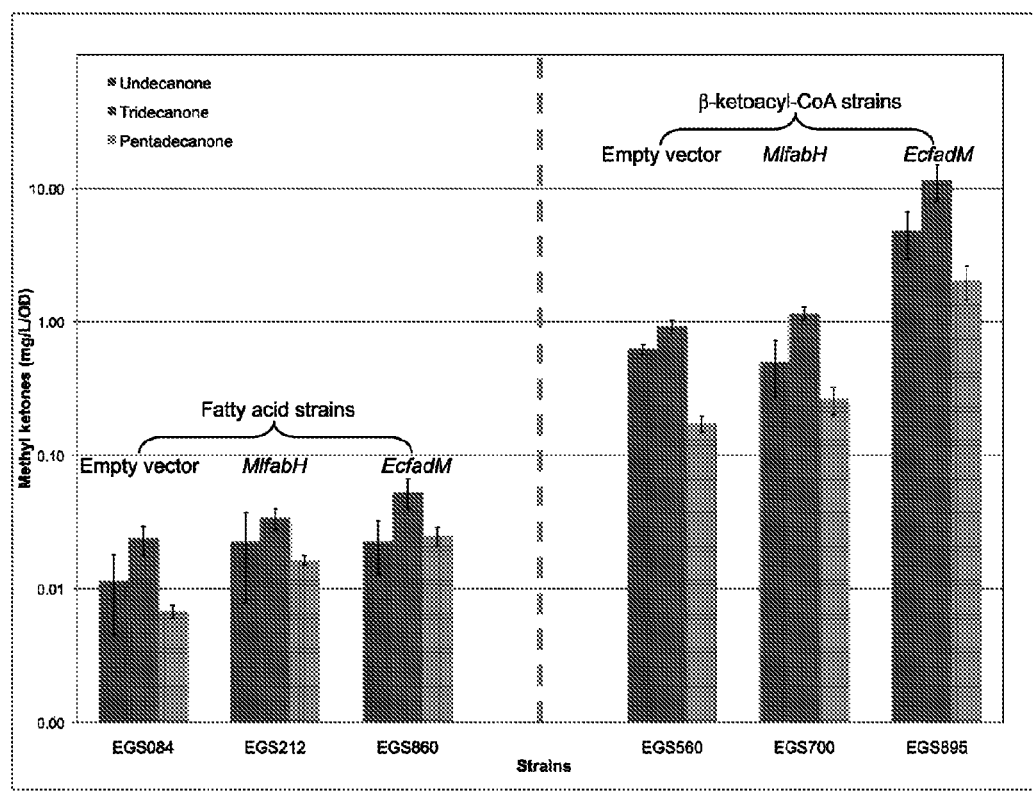
FIG. 5 OD-normalized methyl ketone concentrations in the fatty acid- and β-ketoacyl-CoA-overproducing strains shown in FIG. 1. Bar heights represent the averages of at least three biological replicates and error bars represent one standard deviation.

Detection of methyl ketones in E. coli fatty acid-overproducing strains. Previous studies of alkene biosynthesis in Micrococcus luteus (5) in which M. luteus condensing enzymes [e.g., FabH (β-ketoacyl-ACP synthase III) and FabF (β-ketoacyl-ACP synthase II)] were heterologously expressed in a fatty acid-overproducing strain of E. coli DH1 resulted in unexpected GC/MS detection of methyl ketones. Authentic standards were used to confirm that these compounds were 2-undecanone ($C_{11}$), 2-tridecanone ($C_{13}$; the predominant methyl ketone), and 2-pentadecanone ($C_{15}$). Furthermore, we observed that overexpression of the M. luteus fabH (MlfabH; Mlut_09310) resulted in an increase in methyl ketone concentration relative to the fatty acid-overproducing control strain, particularly on an OD-normalized basis (FIG. 1; FIG. 5).

Enhancement of methyl ketone generation by overproduction of β-ketoacyl-CoAs. Several factors led us to hypothesize that increasing the production of β-ketoacyl-CoAs would lead to better production of methyl ketones: (a) the long-held hypothesis that, in fungi, methyl ketones arise from incomplete β-oxidation of fatty acids and decarboxylation of β-keto acids (10), (b) methyl ketones were observed at higher concentration in fatty acid-overproducing DH1 strains than in wild-type DH1 (data not shown), and (c) the carbon-chain lengths of the observed methyl ketones were consistent with decarboxylation of prominent fatty acids in DH1 (i.e., $C_{12}$, $C_{14}$, and $C_{16}$). To test this hypothesis and increase levels of β-ketoacyl-CoAs, we constructed a modified, truncated fatty acid β-oxidation pathway in DH1 (FIG. 2).

The native fatty acid β-oxidation pathway in E. coli strain DH1 begins with the conversion of free fatty acids into acyl-CoAs by an acyl-CoA synthetase (FadD). The acyl-CoA is then oxidized to a trans-2-enoyl-CoA by a FAD-dependent acyl-CoA dehydrogenase (FadE). Next, FadB catalyzes a hydratase reaction to form a β-hydroxyacyl-CoA, which is then oxidized to a β-ketoacyl-CoA (also catalyzed by the bifunctional FadB). The cycle is completed by CoA-mediated thiolytic cleavage of a β-ketoacyl-CoA to acetyl-CoA and a shorter (n-2) acyl-CoA, a reaction catalyzed by FadA. Our strategy to increase levels of β-ketoacyl-CoAs involved the following steps: (a) overexpression of a heterologous acyl-CoA oxidase used in lieu of FadE, (b) overexpression of the native FadB, and (c) deletion of fadA from the chromosome to truncate the β-oxidation cycle at β-ketoacyl-CoA. We chose to replace FadE with an acyl-CoA oxidase because the latter enzyme is a highly soluble protein (FadE is membrane associated) and has much higher specific activity than FadE (3, 4). Based upon reports of a high-activity acyl-CoA oxidase from Arthrobacter ureafaciens (3), we selected an apparent homolog (Mlut_11700; 63% protein sequence identity) from the related actinobacterium, M. luteus. Both Mlut_11700 and E. coli fadB were cloned into the low-copy pKS1 vector downstream of the 'tesA (thioesterase) gene (Table 1). The chromosomal deletion of fadA in *E. coli* DH1 was performed as described in the Materials and Methods section.

GC/MS analyses of extracts of β-ketoacyl-CoA-overproducing strains indicated dramatic increases in methyl ketone production relative to fatty acid-overproducing strains (e.g., a ~75-fold increase for strain EGS560 versus strain EGS084) (Table 3, FIG. 1). Concentration trends were similar on an OD-normalized basis (compare FIG. 1 and FIG. 5). 2-Tridecanone was the predominant methyl ketone observed in β-ketoacyl-CoA-overproducing strains as it was in fatty acid-overproducing strains (FIG. 1).

Identification of candidate *E. coli* thioesterase genes involved in methyl ketone production. We demonstrated that overproduction of β-ketoacyl-CoAs increased methyl ketone production, however it was unclear whether native *E. coli* proteins were facilitating conversion of the β-ketoacyl-CoAs to methyl ketones (e.g., by hydrolysis of the CoA thioester bond to generate a free β-keto acid and/or decarboxylation of the β-keto acid; FIG. 2). Further investigation of the enhancement of methyl ketone production in the presence of MlfabH suggested that indeed native *E. coli* proteins were facilitating conversion of β-ketoacyl-CoAs to methyl ketones. More specifically, when we mutated the conserved, well-characterized catalytic triad residues (C123S-H275A-N306A) of MlFabH (strain EGS735, Table 1), which should have rendered FabH enzymatically inactive (8), enhancement of methyl ketones was comparable to that observed in the strain expressing wild-type MlFabH (EGS212) (within 10%). This suggested that MlfabH expression had an epigenetic rather than catalytic effect, potentially upregulating native genes whose products facilitated methyl ketone production.

Figure 6:
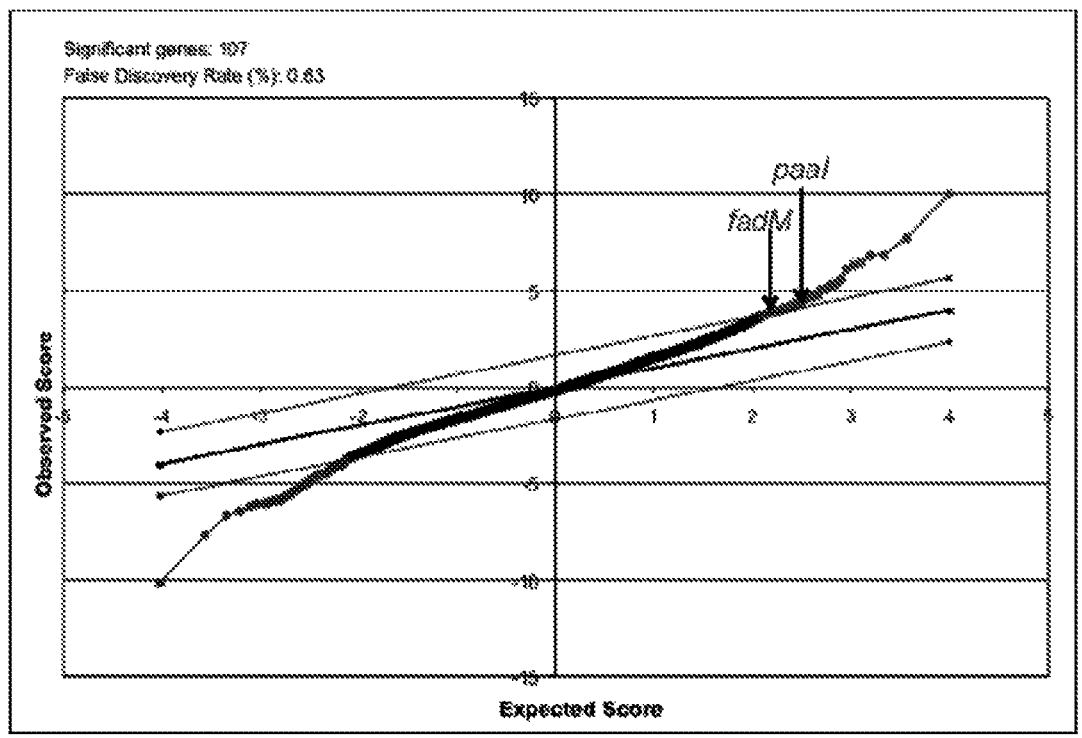
FIG. 6 A graphical representation generated by SAM (Significance Analysis of Microarrays), showing significantly downregulated (green) and upregulated (red) genes in strain EGS212 relative to strain EGS084. The observed relative change in expression (observed score) of each gene is plotted against the expected relative change in expression (expected score) as defined by Tusher et al. (*Proc. Natl. Acad. Sci. USA* 98:5116-21, 2001). Genes above the threshold $(\Delta)^a$ of 1.658 were considered significant and had a $FDR^b$ of 0.63.

To explore the possibility that native *E. coli* DH1 proteins that could facilitate methyl ketone synthesis were being upregulated in the presence of MlfabH, we performed whole-genome transcriptional (microarray) analysis of strains EGS212 (MlfabH; Table 1) and EGS084 (control; empty vector). Using the Significance Analysis of Microarray (SAM) software package, we were able to narrow down the number of significantly upregulated genes to 55 that had a false discovery rate (FDR) of 0.6% or less (FIG. 6 and Table 9). Of these significantly upregulated genes, only 7 were annotated to be associated with metabolism, and two thioesterases (paaI and fadM) were the most upregulated genes in this group (Table 4). RT-qPCR analyses confirmed that fadM was upregulated approximately 2-fold in strain EGS212 compared to strain EGS084.

Overexpression of the *E. coli* fadM thioesterase enhances methyl ketone production. The two thioesterase genes observed to be upregulated in the presence of MlfabH were overexpressed in a fatty acid-overproducing host (fadM in strain EGS860 and paaI in strain EGS790; Table 1) and the effect on methyl ketone production was assessed. Overexpression of paaI slightly decreased methyl ketone production (~30%; data not shown) but overexpression of fadM resulted in approximately a 2-fold increase in 2-tridecanone (relative to the empty-vector control, strain EGS084) (FIG. 1). Furthermore, overexpression of fadM in a β-ketoacyl-CoA-overproducing strain (strain EGS895; Table 1) resulted in a 9-fold increase in total methyl ketone production (relative to the empty-vector control, strain EGS560) (Table 3, FIG. 1).

Figure 3:
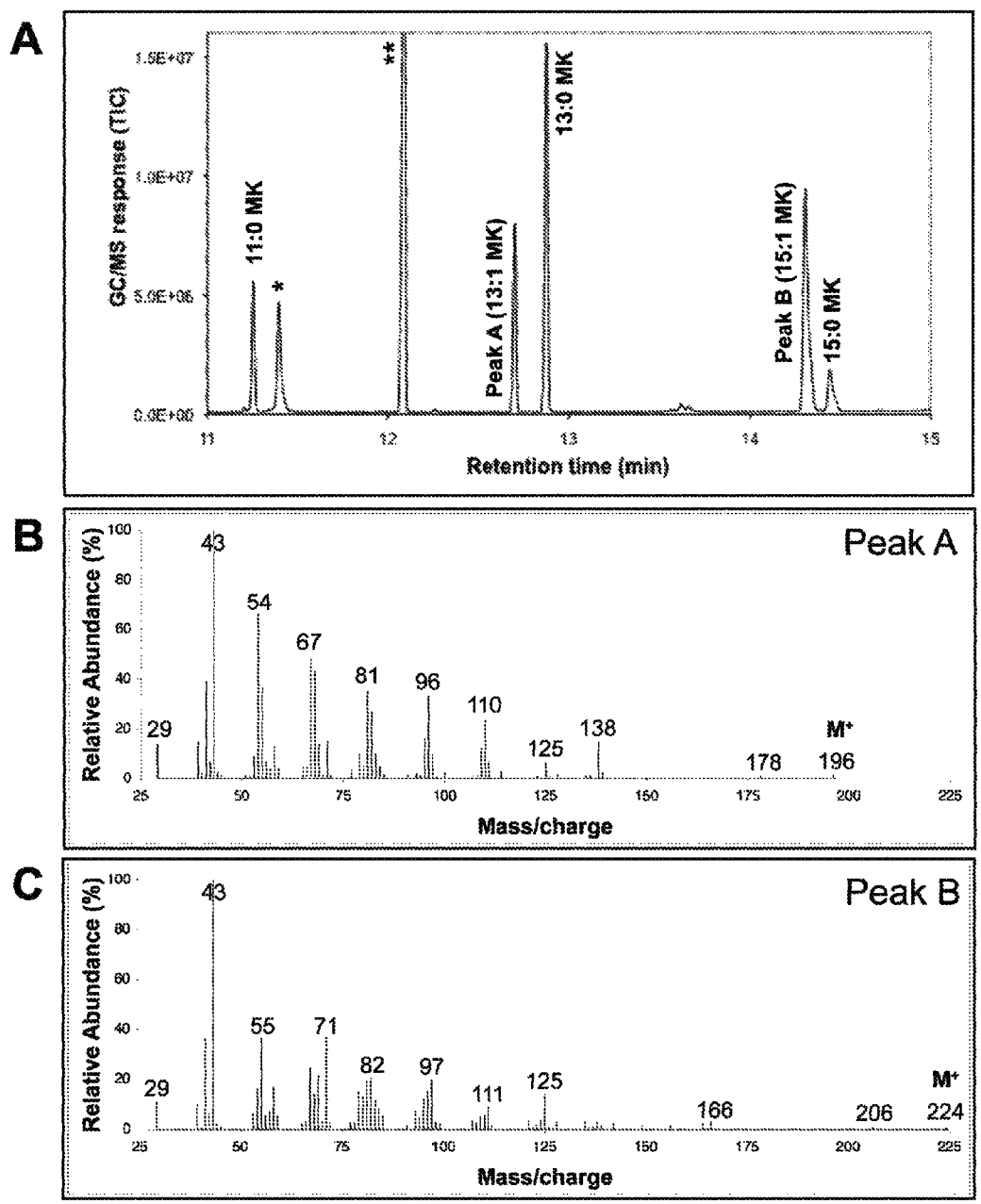
FIG. 3. GC/MS chromatogram of methyl ketone mixture generated by the best producing strain (strain EGS895) and mass spectra of prominent monounsaturated methyl ketones. (A) GC/MS total ion chromatogram (TIC) of diluted decane overlay featuring region with $C_{11}$ to $C_{15}$ saturated and monounsaturated methyl ketones (MK). X:Y notation is described in Table 5. *, component of growth medium. **, hydrocarbon contaminant in decane. (B) 70-eV electron ionization mass spectrum of Peak A, which was identified as tridecenone (see text). (C) 70-eV electron ionization mass spectrum of Peak B, which was identified as pentadecenone (see text).

A broader range of methyl ketones (including monounsaturates) is produced in β-ketoacyl-CoA-overproducing strains expressing FadM. In addition to producing higher concentrations of 2-undecanone, 2-tridecanone, and 2-pentadecanone relative to fatty acid-overproducing strains and/or strains without fadM overexpression (FIG. 1), strain EGS895 also produced a wider range of detectable methyl ketones. This included 2-nonanone ($C_9$) and 2-heptadecanone ($C_{17}$) at low relative concentration (<1% of 2-tridecanone levels) and prominent peaks that are identified as monounsaturated methyl ketones. A representative GC/MS chromatogram of a diluted decane overlay of strain EGS895 is presented in FIG. 3A. Peaks A and B (FIG. 3A) are identified as tridecenone ($C_{13}H_{24}O$) and pentadecenone ($C_{15}H_{28}O$), respectively, based upon electron-ionization GC/MS spectra (FIGS. 3B and C), LC-APCI-TOF MS analysis, and comparison to a pentadecenone standard synthesized in vitro. Although authentic standards are not commercially available for tridecenone and pentadecenone, the TOF-determined accurate masses of the molecular ions representing peaks A and B agreed extremely well (within 0.5 ppm relative error) with the calculated masses for $C_{13}H_{24}O$ and $C_{15}H_{28}O$. Furthermore, the base peak at m/z 43 in both EI spectra (FIG. 3B,C) is consistent with the [$CH_3$—$CO^+$] fragment characteristic of methyl ketones. Finally, an in vitro assay containing the CoA thioester of palmitoleic acid [(Z)-9-hexadecenoic acid), acyl-CoA oxidase (from *M. luteus*), *E. coli* DH1 FadB, and appropriate co-factors resulted in the formation of a compound with an identical GC/MS retention time and mass spectrum as Peak B; this compound was not observed in an assay lacking FadB. Notably, an analogous assay using tetradecanoyl-CoA rather than palmitoleoyl-CoA resulted in the formation of 2-tridecanone. This strongly suggests that Peak B is (Z)-8-pentadecen-2-one (15:1 methyl ketone), which was derived from palmitoleic acid (16:1 fatty acid). By analogy to Peak B, it is logical to conclude that Peak A is (Z)-8-tridecen-2-one derived from myristoleic acid (14:1 fatty acid). However, the mass spectral fragmentation patterns of Peaks A and B differ somewhat in the region between m/z 50 and 120, so the position of the double bond in the tridecenone is less certain.

A summary of the quantitative relationships between methyl ketones (both saturated and unsaturated) and their presumed fatty acid precursors is presented in Table 5. Among the trends apparent from Table 5 is that ratios of fatty acid precursors to the daughter methyl ketones are much greater in fatty acid-overproducing strains (EGS084 and EGS860) than in β-ketoacyl-CoA-overproducing strains (EGS560 and EGS895), suggesting that overall conversion of fatty acids to methyl ketones is far more efficient in the β-ketoacyl-CoA-overproducing strains. In addition, ratios of fatty acid precursors to the daughter methyl ketones are typically lower in strains with overexpressed FadM (EGS860 and EGS895) than in those without (EGS084 and EGS560, respectively), further suggesting that FadM improves the conversion of fatty acids to methyl ketones.

Figure 7:
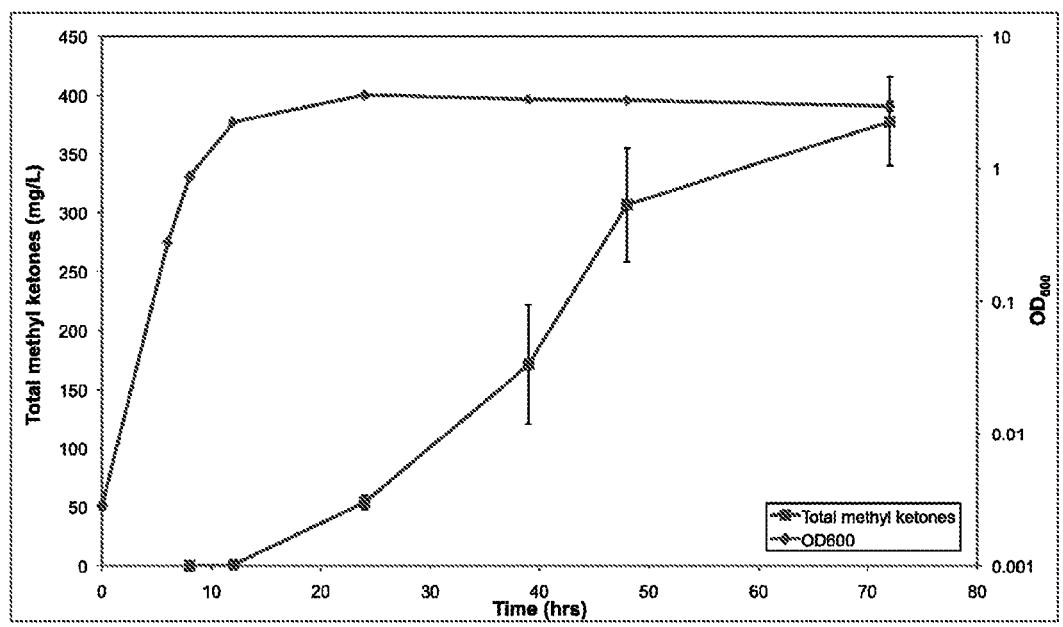
FIG. 7 Methyl ketone production for strain EGS895 in relation to growth (in log-scale). The production curve was generated from 3 biological replicates (freshly transformed).

Further characterization of the best methyl ketone-producing strain (EGS895). The relative distribution of methyl ketones produced by strain EGS895 (the best producing strain in this study) is as follows (expressed as percent of total methyl ketones): 2-undecanone (15%), 2-tridecenone (16%), 2-tridecanone (36%), 2-pentadecenone (26%), 2-pentadecanone (6%). The total concentration of methyl ketones produced by strain EGS895 was 380±38 mg/L for freshly transformed cells (pEG855) and 110±32 mg/L in cells grown from frozen glycerol stocks. A times series of methyl ketone production by strain EGS895 over 72 hr (FIG. 7) indicates that production begins in post-exponential phase and that the production rate decreases between 48 and 72 hr.

Strategies to Modify Methyl Ketone Composition.

Degree of unsaturation and chain length are important factors that mediate key properties of diesel fuels (e.g., low-temperature properties, represented here by melting point, and CN). Three modifications to the genotype or cultivation of strain EGS895 were examined to determine their impact on overall methyl ketone composition and production.

The first strategy involved changing the cultivation temperature of EGS895 to increase degree of unsaturation and thereby decrease melting point. We found that indeed the ratios of the dominant unsaturated methyl ketones ($C_{13}$ and $C_{15}$) to their saturated analogs increased considerably when strain EGS895 was cultivated at lower temperature. To illustrate, at 37° C., the ratio of tridecenone/tridecanone was 0.45, but at 15° C. it increased to 0.93. Similarly, at 37° C., the ratio of pentadecenone/pentadecanone was 4, but at 15° C. it increased to 8.5.

The second strategy was to replace the native 'TesA acyl-ACP thioesterase with UcFatB1 (strain EGS975, Table 1), a plant-derived thioesterase that has a stronger preference toward C12.0 acyl-ACP than does 'TesA (32). Based on the substrate preference of UcFatB1, we anticipated an increase in the proportion of undecanone (derived from $C_{12}$ fatty acid) and a corresponding decrease in melting point. As expected, the ratio of undecanone to tridecanone increased from 0.1 in strain EGS895 to 0.4 in strain EGS975, but unexpectedly the pentadecanone to tridecanone ratio increased from 0.24 in strain EGS895 to 0.82 in strain EGS975.

Although both strategies achieved the intended objective of altering methyl ketone composition, they also resulted in lower total methyl ketone production (from 2- to 5-fold lower) than strain EGS895 cultivated at 37° C. Finally, an attempt was made to increase methyl ketone production by increasing the flux of free fatty acids into the β-oxidation pathway. To accomplish this, *E. coli* FadD (fatty acyl-CoA synthetase; see FIG. 2) was overexpressed in strain EGS895. However, this modification also resulted in a 2-fold decrease rather than an increase in methyl ketone production.

Figure 4:
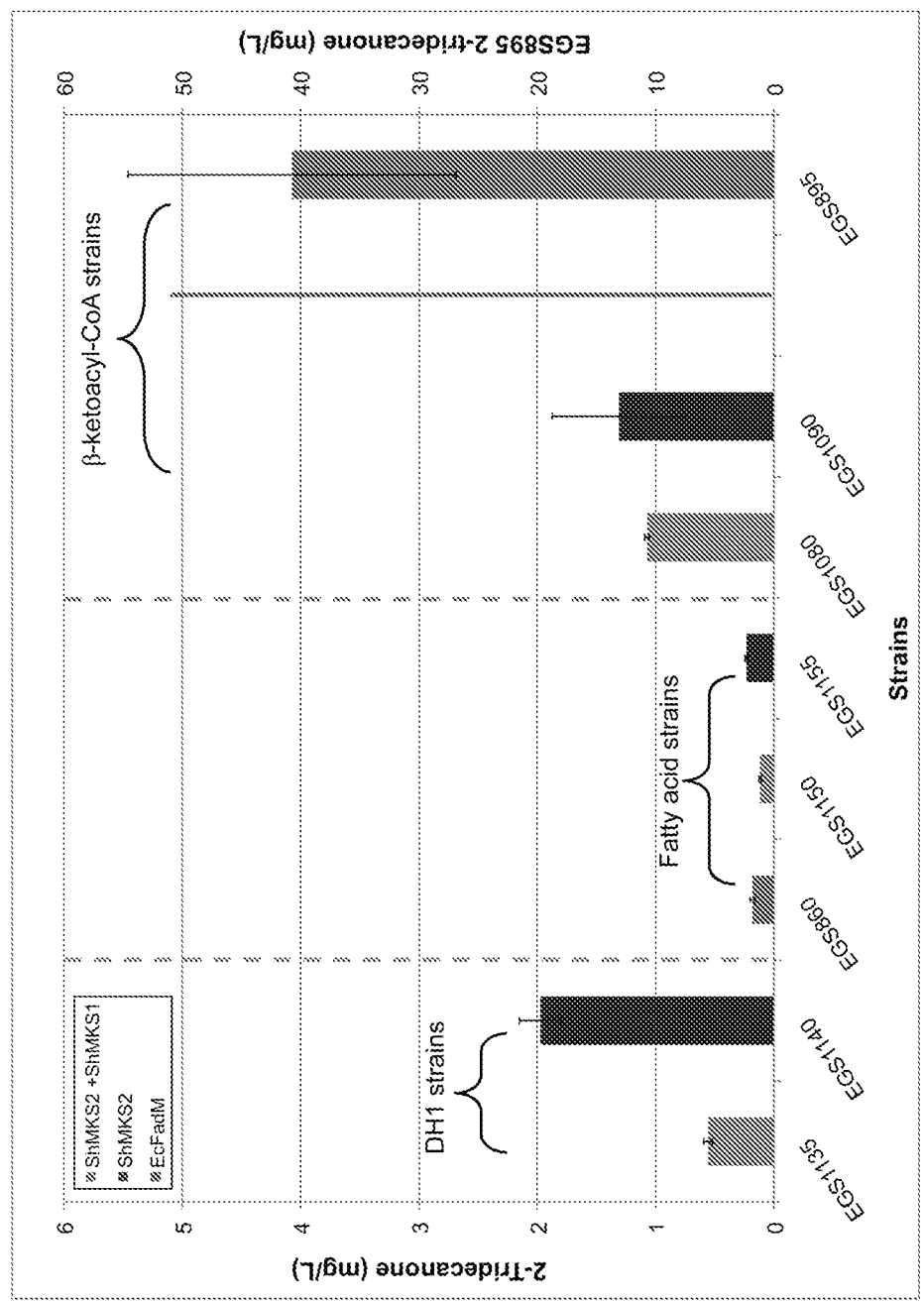
FIG. 4. 2-Tridecanone concentration in DH1 wild-type, fatty acid-overproducing, or β-ketoacyl-CoA-overproducing strains expressing various methyl ketone synthases. Note that the scale for 2-tridecanone concentration in strain EGS895 is on the right-hand y-axis. Bar heights represent averages and error bars represent one standard deviation.

Methyl ketone production in strains containing fadM compared to production in strains containing known methyl ketone synthases. To date, the only proteins that have been experimentally verified as methyl ketone synthases are ShMKS1 and ShMKS2 from *S. habrochaites* and homologous proteins in other plants (6, 31). ShMKS2 has been described as a "hot-dog"-fold-family thioesterase that hydrolyzes β-ketoacyl-ACPs (intermediates of fatty acid biosynthesis) and ShMKS1 is a decarboxylase that acts on β-keto acids (such as those produced by ShMKS2) (31). Since FadM, like ShMKS2, is a thioesterase belonging to the "hot-dog" fold protein family (in this case hydrolyzing long-chain acyl-CoAs) (20), we were curious about the relative effects of overexpression of these proteins on methyl ketone production. Comparisons were made of methyl ketone (2-tridecanone) production in wild-type, fatty acid-overproducing, and β-ketoacyl-CoA-overproducing DH1 strains overexpressing fadM, ShMKS2, or ShMKS1+ShMKS2 (FIG. 4). Proteomics analyses confirmed ample expression of ShMKS1 and ShMKS2 in these studies. In all strains tested, constructs overexpressing ShMKS2 or ShMKS1+ShMKS2 never produced a 2-tridecanone concentration exceeding 5% that of strain EGS895 (a β-ketoacyl-CoA-overproducing, FadM-overexpressing strain). Two aspects of the data in FIG. 4 were unexpected: (a) the best methyl ketone production in a strain containing ShMKS2 was in the wild-type host (strain EGS1140) rather than in a fatty acid- or β-ketoacyl-CoA-overproducing host, and (b) overexpression of ShMKS1 with ShMKS2 never improved methyl ketone production, and in some cases it detracted considerably from methyl ketone production. Regarding the latter point, overexpression of ShMKS1 also detracted from methyl ketone production in strains overexpressing FadM. To illustrate, in β-ketoacyl-CoA-overproducing DH strains overexpressing fadM plus ShMKS1 (with or without its own Pt promoter; strains EGS115 and EGS1120, respectively), 2-tridecanone concentrations were approximately 5-fold lower than in strain EGS895, which did not contain ShMKS1 (data not shown). The reason that ShMKS1 decreased methyl ketone production is unknown.

Strategies to Improve Methyl Ketone Titer.

Additional genetic modifications (Table 6) were made to strain EGS895 that resulted in a methyl ketone titer of more than 800 mg/L (Table 7), representing a titer increase of more than 7-fold relative to strain EGS895. These genetic modifications included: (a) expression of fadR and fadD under the control of a $P_{BAD}$ promoter and (b) knockout of poxB from the DH1 host chromosome. The >800 mg/L titer for strain EGS1370 is the highest methyl ketone titer reported for a bacterium (engineered or wild type).

Effect of Decane Overlay on Production.

In strains with very low methyl ketone production (primarily wild-type *E. coli* DH1), an exhaustive extraction of the cell pellet (using methods described previously (5)) was necessary. However, decane overlays were usable for all other strains. Methyl ketone production was considerably higher when fatty acid- or β-ketoacyl-CoA-overproducing strains were incubated with a decane overlay than when they were sacrificed and the cell pellet exhaustively extracted. To illustrate, for the best producing strain (EGS895; Table 1), the methyl ketone concentration was more than 4-fold greater in the overlay than in the pellet extract at 39 hrs (Table 3). This may be explained by one or more of several factors, including the following: (a) removal of the methyl ketone products provides a thermodynamic driving force for production, (b) the overlay efficiently sequesters methyl ketones that might otherwise be volatilized during cultivation, and (c) removal of methyl ketones (or other metabolites) from the medium may alleviate potentially inhibitory or toxic effects from their accumulation. A comparison between the results of overlay and pellet extractions supports both points (a) and (b). First, the ratio of $C_{14:0}$ fatty acid to $C_{13:0}$ methyl ketone for strain EGS895 was 30-fold lower in overlays than in pellet extractions; this lower ratio in overlays could be explained by more efficient flux of fatty acids to methyl ketones in the presence of the overlay. Second, the ratio of $C_{11:0}$ methyl ketone to $C_{15:0}$ methyl ketone is 2-fold higher for the overlay than for the pellet. Since the $C_{11:0}$ methyl ketone is more volatile than the $C_{15:0}$ methyl ketone, the higher ratio in overlays supports the notion that the decane overlay facilitates capture of volatile compounds that would be lost without an overlay. Regarding the final explanation (toxicity mitigation), this seems unlikely because OD values for strain EGS895 were similar in the presence and absence of an overlay, suggesting that methyl ketones are not particularly toxic (at least, not at these concentrations).

Cetane Number Determination of Selected Methyl Ketones.

Cetane number (CN) is a key index indicating overall diesel fuel quality, much as octane number is a widely used indicator of gasoline fuel quality. More specifically, CN is a measure of ignition delay during compression ignition; a higher CN indicates a shorter ignition delay period and is more favorable than a lower CN (up to a CN of 55 to 60). In the U.S., diesel fuel must have a minimum CN of 40, in accordance with ASTM Standard D975. The CN for 2-undecanone (Sigma) was 56.6 and for a 50/50 (wt/wt) mixture of 2-undecanone and 2-tridecanone was 58.4.

Discussion

We have engineered a small number of modifications into *E. coli* DH1 that resulted in a 700-fold increase in methyl ketone concentration relative to a fatty acid-overproducing strain. Accounting for the use of decane overlays, the overall increase was more than 4500-fold (Table 3). The modifications included overproduction of β-ketoacyl-CoAs (by overexpression of an acyl-CoA oxidase from *M. luteus* and native FadB, as well as chromosomal deletion of fadA) and overexpression of the native thioesterase, FadM. In all host strains tested (wild-type, fatty acid-overproducing, β-ketoacyl-CoA-overproducing DH1), overexpression of the methyl ketone synthase ShMKS2 never produced methyl ketones at concentrations that were more than 5% of those observed for the best-producing FadM-overexpressing strain.

To some extent, the difference in behavior of the two thioesterases, FadM and ShMKS2, can be explained by their known substrates. FadM has relatively high activity on acyl-CoA substrates between $C_{12}$ and $C_{18}$ (particularly 3,5-cis-tetradecadienoyl-CoA) (20), whereas ShMKS2 appears to be well suited to β-ketoacyl-ACPs (31). It follows that a thioesterase that hydrolyzes CoA thioesters (FadM) would be more amenable to acting on β-oxidation intermediates whereas a thioesterase that hydrolyzes ACP thioesters would be more effective at hydrolyzing fatty acid biosynthetic intermediates (β-ketoacyl-ACPs in particular). That said, a limited amount of information is available on the substrate ranges of these two thioesterases (particularly ShMKS2), so the extent to which each favors CoA versus ACP thioesters is unknown (25). Although FadM apparently hydrolyzes β-ketoacyl-CoAs sufficiently to markedly increase methyl ketone yields, it is reported to have considerably (at least 10-fold) higher activity on $C_{16}$ acyl-CoA than on $C_{16}$ β-ketoacyl-CoA (20).

The best methyl ketone producer studied here (strain EGS895) did not have an added decarboxylase to convert free β-keto acids to methyl ketones. Either a native enzyme catalyzed this reaction, or it occurred abiotically, as β-keto acids are well known to be inherently unstable and prone to spontaneous decarboxylation (16). Spontaneous decarboxylation would not be surprising, as we observed substantial methyl ketone yields from in vitro reaction mixtures that produced β-ketoacyl-CoAs from acyl-CoAs; these reaction mixtures lacked both decarboxylases and thioesterases (the only enzymes they contained were acyl-CoA oxidase and FadB). For unknown reasons, overexpression of the ShMKS1 decarboxylase, which is reported to play a role in methyl ketone synthesis in *S. habrochaites*, markedly decreased methyl ketone synthesis in this study (including strains EGS1115 and EGS1120, which were simply ShMKS1-amended versions of EGS895).

As is the case for other fatty acid-derived biofuels, such as fatty acid ethyl esters, saturated, medium-chain methyl ketones addressed in this article have favorable cetane numbers (CN). A less favorable property of the saturated methyl ketones addressed in this article is relatively high melting point (e.g., 30.5° C. for 2-tridecanone; (12)), which is related to cold-temperature diesel fuel properties such as cloud point. This disadvantage could be significantly mitigated by the prominent monounsaturated methyl ketones observed in the best producing strains (monounsaturated methyl ketones account for ~40% of total methyl ketones in strain EGS895). Melting point depression caused by monounsaturation in fatty acid methyl esters illustrates this point. For example, for $C_{16}$ and $C_{18}$ fatty acid methyl esters, the cis-$\Delta^9$ monounsaturated homologs have melting points approximately 60° C. lower than those of their saturated counterparts [the melting point of methyl palmitoleate (16:1) is −33.9° C. whereas that of methyl palmitate (16:0) is 30° C.; the melting point of methyl oleate (18:1) is −19.5° C. whereas that of methyl stearate (18:0) is 39° C.](15). However, unsaturation can also be expected to decrease CN (e.g., a decrease of ~30 in CN applies to $C_{16}$ fatty acid methyl esters; (15)). In addition to degree of unsaturation, chain length will also affect fuel properties (increasing chain length increases CN and melting point). The ensemble of saturated and unsaturated methyl ketones generated by strain EGS895 (and related strains) may have sufficiently favorable collective fuel properties to be appropriate for blending with petroleum-based diesel. Nonetheless, future efforts will be directed at enhancing methyl ketone production (e.g., by enhancing intracellular malonyl-CoA levels; (33)) and modulating the methyl ketone composition to optimize diesel fuel properties.

REFERENCES

1. Antonious, G. F., D. L. Dahlman, and L. M. Hawkins. 2003. Insecticidal and acaricidal performance of methyl ketones in wild tomato leaves. Bull. Environ. Contam. Toxicol. 71:400-7.
2. Baba, T., T. Ara, M. Hasegawa, Y. Takai, Y. Okumura, M. Baba, K. A. Datsenko, M. Tomita, B. L. Wanner, and H. Mori. 2006. Construction of *Escherichia coli* K-12 in-frame, single-gene knockout mutants: the Keio collection. Mol. Syst. Biol. 2:2006.0008.
3. Bakke, M., C. Setoyama, R. Miura, and N. Kajiyama. 2007. N-ethylmaleimide-resistant acyl-coenzyme A oxidase from *Arthrobacter ureafaciens* NBRC 12140: molecular cloning, gene expression and characterization of the recombinant enzyme. Biochim. Biophys. Acta 1774:65-71.
4. Baltazar, M. F., F. M. Dickinson, and C. Ratledge. 1999. Oxidation of medium-chain acyl-CoA esters by extracts of *Aspergillus niger*: enzymology and characterization of intermediates by HPLC. Microbiology 145:271-8.
5. Beller, H. R., E. B. Goh, and J. D. Keasling. 2010. Genes involved in long-chain alkene biosynthesis in *Micrococcus luteus*. Appl. Environ. Microbiol. 76:1212-23.
6. Ben-Israel, I., G. Yu, M. B. Austin, N. Bhuiyan, M. Auldridge, T. Nguyen, I. Schauvinhold, J. P. Noel, E. Pichersky, and E. Fridman. 2009. Multiple biochemical and morphological factors underlie the production of methylketones in tomato trichomes. Plant Physiol. 151:1952-64.
7. Datsenko, K. A., and B. L. Wanner. 2000. One-step inactivation of chromosomal genes in *Escherichia coli* K-12 using PCR products. Proc. Natl. Acad. Sci. USA 97:6640-5.
8. Davies, C., R. J. Heath, S. W. White, and C. O. Rock. 2000. The 1.8 Å crystal structure and active-site architecture of β-ketoacyl-acyl carrier protein synthase III (FabH) from *Escherichia coli*. Structure 8:185-95.
9. Dellomonaco, C., J. M. Clomburg, E. N. Miller, and R. Gonzalez. 2011. Engineered reversal of the beta-oxidation cycle for the synthesis of fuels and chemicals. Nature 476:355-9.
10. Formey, F. W., and A. J. Markovetz. 1971. The biology of methyl ketones. J. Lipid Res. 12:383-95.
11. Fridman, E., J. Wang, Y. Iijima, J. E. Froehlich, D. R. Gang, J. Ohlrogge, and E. Pichersky. 2005. Metabolic, genomic, and biochemical analyses of glandular trichomes from the wild tomato species *Lycopersicon hirsutum* identify a key enzyme in the biosynthesis of methylketones. Plant Cell 17:1252-67.
12. Haynes, W. M. 2010-2011. CRC handbook of chemistry and physics. 91st Edition.
13. Irizarry, R. A., B. Hobbs, F. Collin, Y. D. Beazer-Barclay, K. J. Antonellis, U. Scherf, and T. P. Speed. 2003. Exploration, normalization, and summaries of high density oligonucleotide array probe level data. Biostatistics 4:249-64.
14. Kirchner, O., and A. Tauch. 2003. Tools for genetic engineering in the amino acid-producing bacterium *Corynebacterium glutamicum*. J. Biotechnol. 104:287-99.
15. Knothe, G. 2008. "Designer" biodiesel: optimizing fatty ester composition to improve fuel properties. Energy & Fuels 22:1358-1364.
16. Komberg, A., S. Ochoa, and A. H. Mehler. 1947. Spectrophotometric studies on the decarboxylation of β-keto acids. Fed. Proc. 6:268.
17. Li, M. Z., and S. J. Elledge. 2007. Harnessing homologous recombination in vitro to generate recombinant DNA via SLIC. Nat. Methods 4:251-6.
18. Mendez-Perez, D., M. B. Begemann, and B. F. Pfleger. 2011. Modular synthase-encoding gene involved in α-olefin biosynthesis in *Synechococcus* sp. strain PCC 7002. Appl. Environ. Microbiol. 77:4264-7.
19. Meselson, M., and R. Yuan. 1968. DNA restriction enzyme from *E. coli*. Nature 217:1110-4.
20. Nie, L., Y. Ren, and H. Schulz. 2008. Identification and characterization of *Escherichia coli* thioesterase III that functions in fatty acid β-oxidation. Biochemistry 47:7744-51.
21. Patel, R. N., C. T. Hou, A. I. Laskin, A. Felix, and P. Derelanko. 1980. Microbial oxidation of gaseous hydrocarbons: production of methylketones from corresponding n-alkanes by methane-utilizing bacteria. Appl. Environ. Microbiol. 39:727-33.
22. Rude, M. A., T. S. Baron, S. Brubaker, M. Alibhai, S. B. Del Cardayre, and A. Schirmer. 2011. Terminal olefin (1-alkene) biosynthesis by a novel P450 fatty acid decarboxylase from *Jeotgalicoccus* species. Appl. Environ. Microbiol. 77:1718-27.
23. Sambrook, J., E. F. Fritsch, and T. Maniatis. 1989. Molecular cloning: a laboratory manual, 2nd ed. Cold Spring Harbor Laboratory, Cold Spring Harbor, N.Y.
24. Schirmer, A., M. A. Rude, X. Li, E. Popova, and S. B. del Cardayre. 2010. Microbial biosynthesis of alkanes. Science 329:559-62.
25. Spencer, A. K., A. D. Greenspan, and J. E. Cronan, Jr. 1978. Thioesterases I and II of *Escherichia coli*. Hydrolysis of native acyl-acyl carrier protein thioesters. J. Biol. Chem. 253:5922-6.
26. Steen, E. J., Y. Kang, G. Bokinsky, Z. Hu, A. Schirmer, A. McClure, S. B. Del Cardayre, and J. D. Keasling. 2010. Microbial production of fatty-acid-derived fuels and chemicals from plant biomass. Nature 463:559-62.
27. Studier, F. W., and B. A. Moffatt. 1986. Use of bacteriophage T7 RNA polymerase to direct selective high-level expression of cloned genes. J. Mol. Biol. 189:113-30.
28. Sukovich, D. J., J. L. Seffernick, J. E. Richman, J. A. Gralnick, and L. P. Wackett. 2010. Widespread head-to-head hydrocarbon biosynthesis in bacteria and role of OleA. Appl. Environ. Microbiol. 76:3850-62.
29. Tusher, V. G., R. Tibshirani, and G. Chu. 2001. Significance analysis of microarrays applied to the ionizing radiation response. Proc. Natl. Acad. Sci. USA 98:5116-21.
30. Williams, C. G. 1858. On the constitution of the essential oil of rue. Philosophical Transactions of the Royal Society of London 148:199-204.
31. Yu, G., T. T. Nguyen, Y. Guo, I. Schauvinhold, M. E. Auldridge, N. Bhuiyan, I. Ben-Israel, Y. Iijima, E. Fridman, J. P. Noel, and E. Pichersky. 2010. Enzymatic functions of wild tomato methylketone synthases 1 and 2. Plant Physiol. 154:67-77.
32. Yuan, L., T. A. Voelker, and D. J. Hawkins. 1995. Modification of the substrate specificity of an acyl-acyl carrier protein thioesterase by protein engineering. Proc. Natl. Acad. Sci. USA 92:10639-43.
33. Zha, W., S. B. Rubin-Pitel, Z. Shao, and H. Zhao. 2009. Improving cellular malonyl-CoA level in *Escherichia coli* via metabolic engineering. Metab. Eng. 11:192-8.
34. Zhou, K., L. Zhou, Q. Lim, R. Zou, G. Stephanopoulos, and H. P. Too. 2011. Novel reference genes for quantifying transcriptional responses of *Escherichia coli* to protein overexpression by quantitative PCR. BMC Mol. Biol. 12:18.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

TABLE 1

Bacterial strains, plasmids and primers used in this study

| Strain or plasmid | Relevant Characteristics | Source or reference |
|---|---|---|
| *E. coli* strains | | |
| BL21 (DE3) | F$^-$ ompT gal dcm lon hsdSB($r_B^-$ $m_B^-$) λ(DE3) | (27) |
| DH1 | endA1 recA1 gyrA96 thi-1 glnV44 relA1 hsdR17($r_K^-$ $m_K^+$) λ$^-$ | (19) |
| LT-ΔfadE | DH1 ΔfadE with pKS1 | (26) |
| EGS084 | LT-ΔfadE with pEC-XK99E | (5) |
| EGS212 | LT-ΔfadE with pEG205 | (5) |
| EGS514 | BL21(DE3) with pEG513 | This study |
| EGS517 | BL21(DE3) with pEG516 | This study |
| EGS522 | DH1; ΔfadE; ΔfadA | This study |
| EGS560 | EGS522 with pEG530 & pEC-XK99E | This study |
| EGS700 | EGS522 with pEG530 & pEG205 | This study |
| EGS735 | LT-ΔfadE with pEG705 | This study |
| EGS790 | LT-ΔfadE with pEG775 | This study |
| EGS860 | LF-ΔfadE with pEG855 | This study |
| EGS895 | EGS522 with pEG530 & pEG855 | This study |
| EGS975 | EGS522 with pEG955 & pEG855 | This study |
| EGS1015 | EGS522 with pEG530 & pEG990 | This study |
| EGS1080 | EGS522 with pEG530 & pEG1065 | This study |
| EGS1085 | EGS522 with pEG530 & pEG1070 | This study |
| EGS1090 | EGS522 with pEG530 & pEG1075 | This study |
| EGS1115 | EGS522 with pEG530 & pEG1101 | This study |
| EGS1120 | EGS522 with pEG530 & pEG1106 | This study |
| EGS1135 | DH1 with pEG1065 | This study |
| EGS1140 | DH1 with pEG1075 | This study |
| EGS1150 | LT-ΔfadE with pEG1065 | This study |
| EGS1155 | LT-ΔfadE with pEG1075 | This study |

TABLE 1-continued

Bacterial strains, plasmids and primers used in this study

| Strain or plasmid | Relevant Characteristics | Source or reference |
|---|---|---|
| *M. luteus* strains | | |
| ATCC 4698 | Wild type | ATCC |
| Plasmids | | |
| pEC-XK99E | Km$^r$; *E. coli* - *C. glutamicum* shuttle expression vectors based on the medium copy number plasmid pGA1 and containing the trc promoter | (14) |
| pKS1 | Cm$^r$; p15a derivative containing 'tesA under the lacUV5 promoter | (26) |
| pKS104 | Amp$^r$, ColE1 derivative with fadD (M335I), atf4 under the lacUV5 promoter | (26) |
| pSKB3 | Km$^r$; A derivative of the expression vector pET-28a with the thrombin protease site replaced by a TEV protease site. | Burley[a] |
| pEG205 | Km$^r$; ~1-kb fragment of Mlut_09310 (MlfabH) cloned into pEC-XK99E at EcoRI and XbaI sites. | (5) |
| pEG513 | Km$^r$; ~2.2-kb fragment of fadB (EcDH1_4135) cloned into pSKB3 at NdeI and SalI sites. | This study |
| pEG516 | Km$^r$; ~2.1-kb fragment of Mlut_11700 cloned into pSKB3 at NdeI and SalI sites. | This study |
| pEG530 | Cm$^r$; ~2.1-kb fragment of Mlut_11700 and ~2.2-kb fragment of fadB (EcDH1_4135) cloned downstream of the 'tesA gene in pKS1 by SLIC. | This study |
| pEG705 | Km$^r$; QuikChange mutagenesis of MlfabH in pEG205 to the following residues: C123S, H275A, and N306A. | This study |
| pEG775 | Km$^r$; ~0.4-kb fragment of paaI (EcDH1_2249) cloned into pEC-XK99E at EcoRI and XbaI sites. | This study |
| pEG855 | Km$^r$; ~0.4-kb fragment of fadM (EcDH1_3166) cloned into pEC-XK99E at EcoRI and XbaI sites. | This study |
| pEG955 | Cm$^r$; ~2.2-kb fragment of L-mbp-UCfatB1, ~2.1-kb fragment of Mlut_11700 and 2.2-kb fragment of fadB cloned into pKS1 (digested with MfeI and SalI to remove 'tesA) by SLIC. | This study |
| pEG990 | Km$^r$; ~1.7-kb fragment of fadD M335I allele from pKS104 cloned downstream of fadM in pEG855 by SLIC. | This study |
| pEG1065 | Km$^r$; ~0.8-kb fragment of ShMKS1 and ~0.6-kb fragment of ShMKS2 cloned into pEC-XK99E at BamHI and XbaI sites by SLIC. | This study |
| pEG1070 | Km$^r$; ~0.8-kb fragment of ShMKS1 cloned into pEC-XK99E at BamHI and XbaI sites. | This study |
| pEG1075 | Km$^r$; ~0.6-kb fragment of ShMKS2 cloned into pEC-XK99E at BamHI and XbaI sites. | This study |
| pEG1101 | Km$^r$; ~0.9-kb fragment of p$_{trc}$-ShMKS1 cloned downstream of fadM in pEG855 by SLIC. | This study |
| pEG1106 | Km$^r$; ~0.8-kb fragment of ShMKS1 cloned downstream of fadM in pEG855 by SLIC. | This study |
| pEG1145 | Km$^r$; ~1.2-kb fragment of hcaT (EcDH1_1132) into pEC-XK99E at EcoRI and XbaI sites. | This study |

[a] Stephen K. Burley

TABLE 2

Primers used in this study

| Target genes | Primer name (SEQ ID NO:) | Primer Sequence[a,b] (5'→3') |
|---|---|---|
| Primers used for target gene amplification | | |
| fadB | DH1_fadB_SLIC_F1 (4) | GCGAAGCAGTTGCAGCCTTTAGTAAATCATGACTCATAAGAGCTCGGTACGACCAGATCACCTTGCGG |
| | DH1_fadB_SLIC_R1 (5) | TGGACGGTCATGACGATGCTCCTGTTCGTGAGTGGGGGCGTTCGAACGGCCCATCGGGGT |
| | DH1_fadB_F1 (6) | CTGCCATATGCTTTACAAAGGCGACACCCTGT |
| | DH1_fadB_R1 (7) | TACAGAATTCGAACGGCCCATCGGGGTG |
| fadM | DH1_fadM_F1 (8) | CGCTGAATTCACAACGTAAGGTTATTGCGCTATGC |
| | DH1_fadM_R1 (9) | ATGTTCTAGACTTGAGCATCCGGCACCACAAAAC |
| hcaT | DH1_hcaT_F1 (10) | TACTGAATTCCCTGACGGGAGGGACTCATGGT |
| | DH1_hcaT_R1 (11) | GCTATCTAGAGGAGCAGATCCGCAAAATGCTCG |
| l-mbp | L-mbp_SLIC_F1 (12) | TGTGGAATTGTGAGCGGATAACAATTGCACCAACAAGGACCATAGCATATGAAAATCGAAGAAGGTAAACTGGT |
| | L-mbp_SLIC_R1 (13) | AAGGCGCTTGCCAGGCTCGTCGTTGCCATCCCGAGGTTGTTGTTATTGTTATTGTTG |
| paaI | DH1_paaI_F1 (14) | AGTGGAATTCGGGCGCTTCTGGAGAGCGGTTA |
| | DH1_paaI_R1 (15) | TTATTCTAGAGGCTTCACGCATCAGGCTTCTCC |
| ptrc | Ptrc_SLIC_F1 (16) | GTTTTGTGGTGCCGGATGCTCAAGTCTAGATATCATCGACTGCACGGTGC |
| | Ptrc_SLIC_R1 (17) | TTCCATGTTTCCTCCTGCGCAGGGAATTCCATGGTCTGTTTCCTGTGTGA |

TABLE 2-continued

Primers used in this study

| Target genes | Primer name (SEQ ID NO:) | Primer Sequence[a,b] (5'→3') |
|---|---|---|
| ShMKS1 | MKS1_SLIC_F1(MKS2) (18) | CTGCCAGCATCATCTGTAATCTAGACCTGC GCAGGAGGAAACATGGAA |
|  | MKS1_SLIC_F2(fadM) (19) | TTTTGTGGTGCCGGATGCTCAAGTCTAGAC CTGCGCAGGAGGAAACATGGAA |
|  | MKS1_SLIC_F3(ptrc) (20) | TCACACAGGAAACAGACCATGGAATTCCCT GCGCAGGAGGAAACATGGAA |
|  | MKS1_SLIC_R1 (21) | GCCAAGCTTGCATGCCTGCAGGTCGACTCA TTTGTATTTATTAGCGATGG |
| ShMKS2 | MKS2_SLIC_F1 (22) | TCACACAGGAAACAGACCATGGGATCCCCT GCGCAGGAGGAAACATGTCAC |
|  | MKS2_SLIC_R1 (23) | TTCCATGTTTCCTCCTGCGCAGGTCTAGAT TACAGATGATGCTGGACG |
| Mlut_09310 | Mlut_09310_C123S_F1 (24) | TCTCCGCCGCGAGCGCCGGCTAC |
|  | Mlut_09310_C123S_R1 (25) | GTAGCCGGCGTCGCGGCGGAGA |
|  | Mlut_09310_H275A_F1 (26) | CCGCGTTCATCCCGGCCCAGGCCAACATGC |
|  | Mlut_09310_H275A_R1 (27) | GCATGTTGGCCTGGGCCGGGATGAACGCGG |
|  | Mlut_09310_N306A_F1 (28) | GCGGACGCCGGCGCCACGTCGGCCGC |
|  | Mlut_09310_N306A_R1 (29) | GCGGCCGACGTGGCGCCGGCGTCCGC |
| Mlut_11700 | Mlut_11700_SLIC_F1 (30) | GTCATTGTCGATGCAATTCGCACCCCGATG GGCCGTTCGAACGCCCCCACTCACGAACAG G |
|  | Mlut_11700_SLIC_R1 (31) | TGCCTCTAGCACGCGTCTCACTATAGGGCG AATTGGAGCTCCACCGCGAGGTGACGGGG |
|  | Mlut_11700_F2 (32) | GATTCATATGACCGTCCACGAGAAGCTCGC |
|  | Mlut_11700_R2 (33) | GATTGAATTCACCGCGAGGTGACGGGGG |
| UcfatB1 | UcfatB1_SLIC_F1 (34) | CAACAATAACAATAACAACAACCTCGGGAT GGCAACGACGAGCCTGGCAAGCGCCTT |
|  | UcfatB1_SLIC_R1 (35) | ATCCGCAAGGTGATCTGGTCGTACGAGCTC TCACACACGCGGTTCAGCCGGAAT |

Primers used for real-time PCR

| fadM | fadM_qPCR_F1 (36) | CCGCTACCTTGAATTTCTCG |
|  | fadM_qPCR_R1 (37) | ACGACGAAGGCGATGTTATG |
| hcaT | hcaT_qPCR_F1 (38) | GCTGATGCTGGTGATGATTG |
|  | hcaT_qPCR_R1 (39) | AGTCGCACTTTGCCGTAATC |

[a]Underlined sequences indicate restriction sites or homology regions used for cloning purposes.
[b]Bold sequences indicate nucleotide changes from wild-type gene to generate site-directed mutations.

TABLE 3

Fold improvements in total methyl ketone production[a] resulting from genetic modifications and the presence of a decane overlay

|  | Strains | Overlay | | |
|---|---|---|---|---|
|  |  | EGS895[b] | EGS560[c] | EGS084[d] |
| Overlay | EGS084 | 700 | 76 |  |
|  | EGS560 | 9.0 |  |  |
|  | EGS895 |  |  |  |
| Pellet[e] | EGS084 | 4600 | 500 | 6.6 |
|  | EGS560 | 61 | 6.6 |  |
|  | EGS895 | 4.7 |  |  |

[a]Ratios of total methyl ketone concentrations at 39 hrs. Individual and total methyl ketone concentrations in these strains are presented in Table 10.
[b]Strain EGS895 - β-Ketoacyl-CoA-overproducing, FadM-overexpressing (full description in Table 1)
[c]Strain EGS560 - β-Ketoacyl-CoA-overproducing control without FadM (full description in Table 1)
[d]Strain EGS084 - Fatty acid-overproducing control without FadM (full description in Table 1)
[e]Cell pellet extracted after incubation, no decane overlay used.

TABLE 4

List of metabolic genes that were significantly upregulated during heterologous expression of MlFabH[a].

| Gene ID | Gene Name | Fold Change | Function |
|---|---|---|---|
| b1396 | paaI | 3.4 | predicted thioesterase[b] |
| b0443 | fadM | 2.3 | long-chain acyl-CoA thioesterase III[b] |
| b0459 | maa | 2.1 | maltose O-acetyltransferase |
| b4040 | ubiA | 2.0 | p-hydroxybenzoate octaprenyltransferase |
| b3769 | ilvM | 2.0 | acetolactate synthase II, small subunit |
| b4039 | ubiC | 1.9 | chorismate pyruvate-lyase |
| b1400 | paaY | 1.7 | predicted hexapeptide repeat acetyltransferase |

[a]Based upon whole-genome microarray analysis of strain EGS212 and control strain EGS084.
[b]The two thioesterase genes used for further characterization are indicated in bold.

TABLE 5

Molar ratios of precursor fatty acids to their daughter methyl ketones in fatty acid- and β-ketoacyl-CoA-overproducing strains of E. coli DH1 with and without fadM overexpression.

| | Strains | $C_{12}$ fatty acid/$C_{11}$ methyl ketone[a] | $C_{14}$ fatty acid/$C_{13}$ methyl ketone | $C_{14:1}$ fatty acid/$C_{13:1}$ methyl ketone[b] | $C_{16}$ fatty acid/$C_{15}$ methyl ketone | $C_{16:1}$ fatty acid/$C_{15:1}$ methyl ketone |
|---|---|---|---|---|---|---|
| low ↓ high | Methyl ketone yield | | | | | |
| | EGS084 | 35 | 112 | NA[c] | 220 | NA |
| | EGS860 | 33 | 30 | 6.2 | 41 | 68 |
| | EGS560 | 0.50 | 0.40 | 0.13 | 0.97 | 0[d] |
| | EGS895 | 0.078 | 0.041 | 0.018 | 0.17 | 0.0052 |

[a]Fatty acids were determined as methyl esters.
[b]"X:Y" notation represents "# carbon atoms:# C=C double bonds"
[c]Not Applicable; unsaturated methyl ketone was not detected.
[d]Fatty acid (16:1) not detected.

TABLE 6

Strains and plasmids used since Goh et al. (2012) publication.

| Strain or plasmid | Relevant characteristics | Source or reference |
|---|---|---|
| E. coli strains | | |
| DH1 | endA1 recA1 gyrA96 thi-1 glnV44 relA1 hsdR17($r_K^-$ $m_K^+$) λ⁻ | (Meselson and Yuan 1968) |
| EGS522 | DH1; ΔfadE; ΔfadA | This study |
| EGS1350 | DH1; ΔfadE; ΔfadA; ΔpoxB | This study |
| EGS1320 | EGS522 with pEG530 & pEG1315 | This study |
| EGS1370 | EGS1350 with pEG530 & pEG1315 | This study |
| Plasmids | | |
| pEC-XK99E | Km$^r$; E. coli - C. glutamicum shuttle expression vectors based on the medium copy number plasmid pGA1 and containing the trc promoter | (Kirchner and Tauch 2003) |
| pKS1 | Cm$^r$; p15a derivative containing 'tesA under the lacUV5 promoter | (Steen, Kang et al. 2010) |
| pE8a-fadR | Amp$^r$; ColE1 plasmid with fadR under the pBad promoter. | (Zhang, Ouellet et al.) |
| pEG530 | Cm$^r$; ~2.1-kb fragment of Mlut_11700 and ~2.2-kb fragment of fadB (EcDH1_4135) cloned downstream of the 'tesA gene in pKS1 by SLIC. | This study |
| pEG855 | Km$^r$; ~0.4-kb fragment of fadM(EcDH1_3166) cloned into pEC-XK99E at EcoRI and XbaI sites. | This study |
| pEG1210 | Km$^r$; ~2.1-kb fragment of araC-pBad-fadR from pE8a-fadR cloned into pEG855 at NdeI by SLIC. | This study |
| pEG1315 | Km$^r$; ~0.6-kb fragment of codon-optimized fadD cloned into pEG1210 at NdeI site by SLIC. | This study |

Kirchner, O. and A. Tauch (2003). "Tools for genetic engineering in the amino acid-producing bacterium Corynebacterium glutamicum." J Biotechnol 104(1-3): 287-99.
Meselson, M. and R. Yuan (1968). "DNA restriction enzyme from E. coli." Nature 217(5134): 1110-4.
Steen, E. J., Y. Kang, et al. (2010). "Microbial production of fatty-acid-derived fuels and chemicals from plant biomass." Nature 463(7280): 559-62.
Zhang, F., M. Ouellet, et al. (2012). "Enhancing fatty acid production by the expression of the regulatory transcription factor FadR." Metab Eng. 14: 653-60.

TABLE 7

Performance of improved methyl ketone-producing strains developed after publication of Goh et al. (2012)[a]

| | EZ Rich[b] with 1% glucose | | M9 with 1% glucose | |
|---|---|---|---|---|
| Strains | Titer (mg/L) | Yield[c] (% of max. theoretical) | Titer (mg/L) | Yield (% of max. theoretical) |
| EGS1320 | 330 ± 220 | 9.4 | 350 ± 7.1 | 10 |
| EGS1370 | 810 ± 81 | 23 | 440 ± 210 | 13 |

[a]Cultures were grown in 250-mL non-baffled Erlenmeyer flasks containing 50 mL of appropriate media at 37° C. with 200-rpm agitation. After 6 hrs of growth, cultures were induced with 0.5 mM IPTG and 2.5 mL of spiked decant overlay was added.
[b]EZ Rich Medium (Teknova, Hollister, CA)
[c]Yield is calculated based on a maximum theoretical yield of 0.35 g of methyl ketones per gram of glucose.

TABLE 8

Codon-optimized nucleotide sequences of the ShMKS1 (SEQ ID NO: 40), ShMKS2 (SEQ ID NO: 41), and UCfatB1 (SEQ ID NO: 43) genes (see Table 1). The boldface sequences indicate restriction sites inserted for cloning purposes and underlined sequences indicate the RBS inserted upstream of the start codon.

>ShMKS1 - 827 bp
GGATCC<u>CCTG CGCAGGAGGA AAC</u>ATGGAAA AATCAATGTC CCGGTTCGTC ANALAACACT TCGTTCTGGT TCATACCGCC

TTTCATGGTG CTTGGTGCTG GTACAAAATC GTGGCACTGA TGCGTAGCTC TGGCCATAAC GTTACCGCCC TGGATCTGGG

CGCATCAGGT ATTAACCCGA ACAGGCGCT GCAAATCCCG AATTTTTCAG ACTATCTGTC GCCGCTGATG GAATTTATGG

CCTCACTGCC GGCAAATGAA AAAATTATCC TGGTGGGTCA CGCACTGGGC GGTCTGGCTA TTTCGAAAGC GATGGAAACC

TABLE 8-continued

Codon-optimized nucleotide sequences of the ShMKS1 (SEQ ID NO: 40), ShMKS2 (SEQ ID NO: 41), and UCfatB1 (SEQ ID NO: 43) genes (see Table 1). The boldface sequences indicate restriction sites inserted for cloning purposes and underlined sequences indicate the RBS inserted upstream of the start codon.

TTTCCGGAAA AAATCAGCGT CGCTGTGTTC CTGTCTGGCC TGATGCCGGG TCCGAACATT GATGCCACCA CGGTTTGCAC

GAAAGCTGGC AGCGGAGTCC TGGGTCAGCT GGACAATTGT GTGACCTATG AAAACGGCCC GACGAATCCG CCGACCACGC

TGATTGCCGG TCCGAAATTT CTGGCAACCA ACGTCTACCA TCTGTCTCCG ATCGAAGATC TGGCACTGGC AACGGCACTG

GTTCGTCCGC TGTATCTGTA CCTGGCGGAA GACATTAGTA AAGAAGTGGT TCTGAGTTCA AACGTTACG GCTCCGTTAA

ACGCGTCTTT ATCGTGGCTA CCGAAAACGA TGCGCTGAAA AAAGAATTTC TGAAACTGAT GATCGAGAAA AACCCGCCGG

ATGAAGTTAA AGAAATCGAA GGTTCCGACC ACGTCACCAT GATGTCAAAA CCGCAACAAC TGTTCACGAC CCTGCTGTCC

ATCGCTAATA AATACAAATG ATCTAGA

>ShMKS2 - 656 bp
GGATCC<u>CCTG CGCAGGAGGA AAC</u>ATGTCAC ACTCTTTCTC AATCGCAACC AACATCCTGC TGCTGAATCA TGGCTCGCCG

CCGTCAACCT TCCCGGTCAT CCCGCATCGC CAGCTGCCGC TGCCGAACCT GCGTCTGAGC AGCCGTAAAA GTCGCTCCTT

TGAAGCACAT AGTGCTTTCG ATCTGAAATC AACCCAGCGC ATGTCGGATC AAGTGTATCA TCACGACGTG AACTGACGG

TTCGTGATTA CGAACTGGAC CAGTTTGGCG TGGTTAACAA TGCGACCTAT GCCTCATACT GCCAACATTG TCGCCACGCA

TTCCTGGAAA AAATTGGCGT TTCGGTCGAT GAAGTCACCC GTAACGGTGA CGCACTGGCA GTGACGGAAC TGAGTCTGAA

ATTTCTGGCG CCGCTGCGCT CCGGCGATCG TTTTGTCGTG CGTGCGCGCC TGTCTCATTT CACGGTTGCC CGCCTGTTTT

TCGAACACTT TATCTTCAAA CTGCCGGACC AAGAACCGAT TCTGGAAGCA CGTGGTATCG CTGTCTGGCT GAATCGTAGC

TATCGCCCGA TTCGTATCCC GTCTGAATTT AATAGTAAAT TCGTCAAATT CCTGCACCAA AAAGTTGTG GCGTCCAGCA

TCATCTGTAA TCTAGA

>UCfatB1 - 1161 bp
GAATTCATGG CAACGACGAG CCTGGCAAGC GCCTTCTGTT CGATGAAAGC TGTTATGCTG GCCCGTGATG GCCGTGGTAT GAAACCGCGT AGCTCAGATC TGCAGCTGCG TGCAGGCAAC GCTCCGACCT CGCTGAAAAT GATCAACGGT ACCAAATTCA GTTACACGGA ATCCCTGAAA CGCCTGCCGG ATTGGAGTAT GCTGTTTGCC GTCATTACCA CGATCTTCTC CGCGGCCGAA AAACAGTGGA CCAACCTGGA ATGGAAACCG AAACCGAAAC TGCCGCAACT GCTGGATGAC CATTTTGGTC TGCACGGCCT GGTTTTTCGT CGCACCTTCG CGATTCGTAG CTATGAAGTC GGCCCGGATC GCTCAACCTC GATCCTGGCC GTGATGAACC ATATGCAGGA AGCGACGCTG AATCACGCCA AAAGCGTGGG TATTCTGGGC GATGGTTTCG GCACCACGCT GGAAATGTCT AAACGTGACC TGATGTGGGT GGTTCGTCGC ACCCATGTCG CAGTGGAACG CTACCCGACC TGGGGCGATA CGGTTGAAGT CGAATGCTGG ATCGGTGCTT CTGGCAACAA TGGTATGCGT CGCGATTTCC TGGTTCGTGA CTGCAAAACC GGTGAAATTC TGACCCGCTG TACGAGCCTG TCTGTGCTGA TGAATACCCG TACGCGTCGC CTGAGTACGA TCCCGGATGA AGTTCGCGGC GAAATTGGTC CGGCATTTAT CGACAACGTG GCTGTTAAAG ATGACGAAAT CAAAAAACTG CAGAAACTGA ACGATAGCAC GGCAGACTAT ATCCAAGGCG GTCTGACGCC GCGTTGGAAC GATCTGGACG TTAATCAGCA TGTGAACAAT CTGAAATACG TCGCGTGGGT GTTTGAAACC GTGCCGGATT CAATTTTCGA ATCGCATCAC ATCAGCTCTT TTACCCTGGA ATACCGTCGC GAATGCACGC GTGATAGCGT GCTGCGCTCT CTGACCACCG TTAGTGGCGG TAGTTCCGAA GCGGGCCTGG TTTGTGACCA CCTGCTGCAA CTGGAAGGCG GTTCCGAAGT CCTGCGTGCC CGCACCGAAT GGCGCCCGAA ACTGACCGAT TCCTTCCGTG

GCATTAGTGT GATTCCGGCT GAACCGCGTG TGTGAGAGCT C

TABLE 9

List of 55 significantly upregulated genes (sorted by d score[a]) in strain EGS212 vs.
strain EGS084 in whole-genome microarray experiments. Significant genes were
determined based on Δ > 1.658 as shown in FIG. 6.

| Gene ID | Gene Name | Score (d) | Fold Change | Annotation |
|---|---|---|---|---|
| b4216 | ytfJ | 10.03 | 2.96 | predicted transcriptional regulator |
| b0537 | intD | 7.71 | 2.80 | DLP12 prophage; predicted integrase |
| b4271 | — | 6.85 | 2.49 | — |
| b1557 | cspB | 6.83 | 6.11 | Qin prophage; cold shock protein |
| b1242 | ychE | 6.47 | 3.94 | predicted inner membrane protein |
| b4595 | yciY | 6.36 | 1.67 | hypothetical protein |
| b3832 | rmuC | 6.09 | 1.78 | predicted recombination limiting protein |
| b1280 | yciM | 5.56 | 2.28 | TPR-repeats-containing protein |
| b3645 | dinD | 5.35 | 2.08 | DNA-damage-inducible protein |
| b3628 | rfaB | 5.32 | 1.81 | UDP-D-galactose:(glucosyl)lipopolysaccharide-1,6-D-galactosyltransferase |
| b1295 | ymjA | 5.18 | 2.48 | predicted protein |
| b2646 | ypjF | 5.08 | 5.84 | CP4-57 prophage; toxin of the YpjF-YfjZ toxin-antitoxin system |
| b4040 | ubiA | 5.06 | 2.03 | p-hydroxybenzoate octaprenyltransferase |
| b0162 | cdaR | 4.77 | 1.66 | DNA-binding transcriptional regulator for gar and gud operons; carbohydrate diacid regulator |
| b1279 | yciS | 4.77 | 1.47 | conserved inner membrane protein |
| b0217 | yafT | 4.74 | 5.98 | lipoprotein |
| b4566 | yjhX | 4.69 | 9.34 | conserved protein |
| b4313 | fimE | 4.68 | 3.67 | tyrosine recombinase/inversion of on/off regulator of fimA |
| b1053 | mdtG | 4.67 | 2.12 | predicted drug efflux system |
| b4307 | yjhQ | 4.64 | 4.70 | KpLE2 phage-like element; predicted acetyltransferase |
| b3096 | mzrA | 4.54 | 2.02 | modulator of EnvZ/OmpR regulon |
| b1978 | yeeJ | 4.44 | 1.97 | probable adhesin |
| b2832 | ygdQ | 4.38 | 2.79 | inner membrane protein, UPF0053 family |
| b4039 | ubiC | 4.37 | 1.93 | chorismate pyruvate-lyase |
| b4545 | — | 4.35 | 4.87 | — |
| b1655 | ydhO | 4.27 | 2.53 | predicted peptidase, C40 clan |
| b1025 | ycdT | 4.21 | 3.73 | diguanylate cyclase |
| b2269 | elaD | 4.21 | 2.90 | protease, capable of cleaving an AMC-ubiquitin model substrate |
| b2295 | yfbV | 4.19 | 1.96 | inner membrane protein, UPF0208 family |
| b0459 | maa | 4.17 | 2.11 | maltose O-acetyltransferase |
| b1400 | paaY | 4.15 | 1.67 | predicted hexapeptide repeat acetyltransferase |
| b3184 | yhbE | 4.15 | 1.56 | conserved inner membrane protein |
| b3630 | rfaP | 4.14 | 1.57 | kinase that phosphorylates core heptose of lipopolysaccharide |
| b3325 | gspD | 4.08 | 2.54 | general secretory pathway component, cryptic |
| b3769 | ilvM | 4.01 | 1.95 | acetolactate synthase II, small subunit |
| b4215 | ytfI | 4.00 | 2.80 | predicted protein |
| b4337 | mdtM | 3.97 | 5.61 | multidrug efflux system protein |
| b0130 | yadE | 3.95 | 1.78 | predicted polysaccharide deacetylase lipoprotein |
| b3216 | yhcD | 3.94 | 1.82 | predicted outer membrane fimbrial subunit usher protein |
| b0702 | ybfB | 3.94 | 3.52 | predicted membrane protein |
| b1396 | paaI | 3.93 | 3.43 | predicted thioesterase |
| b4306 | yjhP | 3.92 | 3.88 | KpLE2 phage-like element; predicted methyltransferase |
| b3546 | eptB | 3.91 | 2.43 | KDO phosphoethanolamine transferase, $Ca^{2+}$-inducible |
| b1558 | cspF | 3.90 | 6.34 | Qin prophage; cold shock protein |
| b3406 | greB | 3.90 | 1.54 | transcript cleavage factor |
| b2124 | yehS | 3.87 | 1.73 | conserved protein, DUF1456 family |
| b3624 | rfaZ | 3.86 | 2.69 | lipopolysaccharide core biosynthesis protein |
| b3627 | rfaI | 3.84 | 2.18 | UDP-D-galactose:(glucosyl)lipopolysaccharide-alpha-1,3-D-galactosyltransferase |
| b1210 | hemA | 3.83 | 1.69 | glutamyl tRNA reductase |
| b3989 | yjaZ | 3.82 | 2.41 | stationary phase growth adaptation protein |
| b0443 | fadM | 3.82 | 2.28 | long-chain acyl-CoA thioesterase III |
| b4305 | sgcX | 3.82 | 1.87 | KpLE2 phage-like element; predicted endoglucanase with Zn-dependent exopeptidase domain |
| b1620 | malI | 3.81 | 1.60 | transcriptional repressor of Mal regulon |
| b1135 | rluE | 3.80 | 1.96 | 23S rRNA U2457 pseudouridine synthase |
| b3348 | slyX | 3.79 | 2.06 | protein required for phi X174 lysis |

[a]d is the observed score, which is determined by the ratio of change in gene expression to standard deviation (see FIG. 6).

TABLE 10

Individual and summed methyl ketone concentrations produced by selected *E. coli* strains (see Table 1 for descriptions) assayed with decane overlays (at 39 or 72 hr) or extractions of cell pellets (at 39 hr). The number of biological replicates is indicated in parenthesis after the strain name. Total methyl ketones from 39-hr overlays and pellet extracts were used to determine the fold changes shown in Table 3.

| Strains | Undecanone (mg/L) | Tridecanone (mg/L) | Pentadecanone (mg/L) | Tridecenone (mg/L) | Pentadecenone (mg/L) | Total methyl ketones (mg/L) |
|---|---|---|---|---|---|---|
| EGS84[a] 72 hr (3) | 0.03 ± 0.02 | 0.07 ± 0.02 | 0.02 ± 0.001 | ND | ND | 0.12 ± 0.04 |
| EGS560[a] 72 hr (3) | 2.4 ± 0.4 | 3.5 ± 0.3 | 0.7 ± 0.1 | 1.7 ± 0.3 | 1.9 ± 0.1 | 10.0 ± 0.73 |
| EGS895[a] 72 hr (5) | 17 ± 8 | 41 ± 14 | 7.2 ± 2.6 | 18 ± 7 | 29 ± 7 | 110 ± 32 |
| EGS84[a] 39 hr (3) | 0.06 ± 0.07 | 0.05 ± 0.02 | 0.02 ± 0.02 | ND | ND | 0.12 ± 0.09 |
| EGS560[a] 39 hr (3) | 1.4 ± 0.4 | 3.9 ± 1.3 | 0.83 ± 0.42 | 1.4 ± 0.2 | 1.9 ± 0.7 | 9.5 ± 2.8 |
| EGS895[a] 39 hr (5) | 12 ± 5 | 38 ± 12 | 8.3 ± 3.1 | 15 ± 8 | 15 ± 9 | 88 ± 38 |
| EGS084 pellet (5) | ND | 0.02 ± 0.01 | ND | ND | ND | 0.02 ± 0.01 |
| EGS560 pellet (3) | 0.07 ± 0.02 | 0.4 ± 0.05 | 0.15 ± 0.05 | 0.26 ± 0.05 | 0.54 ± 0.15 | 1.4 ± 0.3 |
| EGS895 pellet (3) | 1.7 ± 1.0 | 5.0 ± 2.1 | 1.7 ± 0.5 | 4.1 ± 1.4 | 6.4 ± 3.2 | 19 ± 7 |

[a]Decane overlay

Illustrative Enzyme Sequences:

*E. coli* FadM polypeptide sequence, accession number ACX40792.1

SEQ ID NO: 1

MQTQIKVRGYHLDVYQHVNNARYLEFLEEARWDGLENSDSFQWMTAH
NIAFVVVNININYRRPAVLSDLLTITSQLQQLNGKSGILSQVITLEP
EGQVVADALITFVCIDLKTQKALALEGELREKLEQMVK

*Micrococcus luteus* NCTC 2665 acyl-CoA oxidase polypeptide sequence, accession number YP_002957230.1

SEQ ID NO: 2

MTVHEKLAPQSPTHSTEVPTDVAEIAPERPTPGSLDAAALEEALLGR
WAAERRESRELAKDPALWRDPLLGMDEHRARVLRQLGVLVERNAVHR
AFPREFGGEDNHGGNISAFGDLVLADPSLQIKAGVQWGLFSSAILHL
GTAEHHRRWLPGAMDLSVPGAFAMTEIGHGSDVASIATTATYDEATQ
EFVIHTPFKGAWKDYLGNAALHGRAATVFAQLITQGVNHGVHCFYVP
IRDEKGAFLPGVGGEDDGLKGGLNGIDNGRLHFTQVRIPRTNLLNRY
GDVAEDGTYSSPIASPGRRFFTMLGTLVQGRVSLSLAATTASFLGLI
IGALAYAEQRRQFNASDPQREEVLLDYQNHQRRLIDRLARAYADAFA
SNELVVKFDDVFSGRSDTDVDRQELETLAAAVKPLTTWHALDTLQEA
REACGGAGFLAENRVTQMRADLDVYVTFEGDNTVLLQLVGKRLLTDY
SKEFGRLNVGAVSRYVVHQASDAIHRAGLHKAVQSVADGGSERRSAN
WFKDPAVQHELLTERVRAKTADVAGTLSGARGKGQAAQAEAFNTRQH
ELIEAARNHGELLQWEAFTRALEGITDETTKTVLTWLRDLFALRLIE
DDLGWFVAHGRVSSQRARALRGYVNRLAERLRPFALELVEAFGLEPE
HLRMAVATDAETQRQEEAHAWFTARRAAGEEPEDEKAVRAREKAARG
RRG

*E. coli* DH1 FadB polypeptide sequence, accession number ACX41735.1

SEQ ID NO: 3

MLYKGDTLYLDWLEDGIAELVFDAPGSVNKLDTATVASLGEAIGVLE
QQSDLKGLLLRSNKAAFIVGADITEFLSLFLVPEEQLSQWLHFANSV
FNRLEDLPVPTIAAVNGYALGGGCECVLATDYRLATPDLRIGLPETK
LGIMPGFGGSVRMPRMLGADSALEIIAAGKDVGADQALKIGLVDGVV
KAEKLVEGAKAVLRQAINGDLDWKAKRQPKLEPLKLSKIEATMSFTI
AKGMVAQTAGKHYPAPITAVKTIEAAARFGREEALNLENKSFVPLAH
TNEARALVGIFLNDQYVKGKAKKLTKDVETPKQAAVLGAGIMGGGIA
YQSAWKGVPVVMKDINDKSLTLGMTEAAKLLNKQLERGKIDGLKLAG
VISTIHPTLDYAGFDRVDIVVEAVVENPKVKKAVLAETEQKVRQDTV
LASNTSTIPISELANALERPENFCGMHFFNPVHRMPLVEIIRGEKSS
DETIAKVVAWASKMGKTPIVVNDCPGFFVNRVLFPYFAGFSQLLRDG
ADFRKIDKVMEKQFGWPMGPAYLLDVVGIDTAHHAQAVMAAGFPQRM
QKDYRDAIDALFDANRFGQKNGLGFWRYKEDSKGKPKKEEDAAVEDL
LAEVSQPKRDFSEEEIIARMMIPMVNEVVRCLEEGIIATPAEADMAL
VYGLGFPPFHGGAFRWLDTLGSAKYLDMAQQYQHLGPLYEVPEGLRN
KARHNEPYYPPVEPARPVGDLKTA

What is claimed is:

1. A genetically modified bacterial host cell that produces methyl ketones, wherein the genetically modified bacterial host cell comprises a recombinant nucleic acid construct encoding a FadM that is capable of converting a β-ketoacyl-CoA to a β-keto acid, and overproduces β-ketoacyl-CoAs compared to a control bacterial host cell that has not been transformed with the nucleic acid construct encoding the FadM, wherein the FadM comprises an amino acid sequence having at least 60% identity to SEQ ID NO:1, and further, wherein the genetically modified host cell:
   comprises a recombinant nucleic acid sequence that encodes an acyl-CoA oxidase capable of converting an acyl-CoA to a trans-2-enoyl-CoA;
   comprises a recombinant nucleic acid sequence that encodes a FadB capable of converting a trans-2-enoyl-CoA to a β-hydroxyacyl-CoA and a β-hydroxyacyl-CoA to a β-ketoacyl-CoA; and
   has an inactive fadA gene or chromosomal deletion of all or part of the fadA gene such that the host cell does not express active FadA.

2. The genetically modified host cell of claim 1, wherein the FadM has at least 70% amino acid sequence identity to SEQ ID NO:1.

3. The genetically modified host cell of claim 1, wherein the FadM is an *E. coli* FadM.

4. The genetically modified host cell of claim 1, wherein the acyl-CoA oxidase has at least 60% amino acid sequence identity to SEQ ID NO:2.

5. The genetically modified host cell of claim 4, wherein the acyl-CoA oxidase is from *Micrococcus luteus*.

6. The genetically modified host cell of claim 1, wherein the genetically modified host cell further comprises a recombinant nucleic acid sequence that encodes a cytoplasmically-directed thioesterase 'tesA gene.

7. The genetically modified host cell of claim 1, wherein the genetically modified host cell has an inactive fadE gene or chromosomal deletion of all or part of the fadE gene such that the host cell does not express active FadE.

8. The genetically modified host cell of claim 1, wherein the host cell has an inactive poxB gene or chromosomal deletion of all or part of the poxB gene such that the host cell does not express PoxB.

9. The genetically modified host cell of claim 1, wherein the host cell further comprises a recombinant nucleic acid sequence that is capable of expressing FadR and a recombinant nucleic acid sequence that is capable of expressing FadD.

10. The genetically modified host cell of claim 8, wherein the host cell further comprises a recombinant nucleic acid sequence that is capable of expressing FadR and a recombinant nucleic acid sequence that is capable of expressing FadD.

11. The genetically modified host cell of claim 1, wherein the host cell is a bacterial cell selected from the *Escherichia, Enterobacter, Azotobacter, Erwinia, Bacillus, Pseudomonas, Klebsielia, Proteus, Salmonella, Serratia, Shigella, Ralstonia, Rhizobia,* or *Vitreoscilla* taxonomical class.

12. The genetically modified host cell of claim 11, wherein the bacterial cell is an *Escherichia coli* cell.

13. A method of enhancing production of methyl ketones, the method comprising culturing the genetically modified host cell of claim 1 under conditions such that the culturing results in the production of methyl ketones.

14. The method of claim 13, further comprising recovering the methyl ketones using a decane overlay.

15. A genetically modified bacterial host cell that produces methyl ketones, wherein the genetically modified bacterial host cell:
   comprises a recombinant nucleic acid construct that comprises a nucleic acid sequence that encodes a FadM that is capable of converting a β-ketoacyl-CoA to a β-keto acid, wherein the FadM has at least 60% identity to SEQ 1,
   comprises a recombinant nucleic acid sequence that encodes an acyl-CoA oxidase capable of converting an acyl-CoA to a trans-2-enoyl-CoA;
   comprises a recombinant nucleic acid sequence that encodes a FadB capable of converting a trans-2-enoyl-CoA to a β-hydroxyacyl-CoA and a β-hydroxyacyl-CoA to a β-ketoacyl-CoA;
   comprises a recombinant nucleic acid sequence that is capable of expressing FadR and a recombinant nucleic acid sequence that is capable of expressing FadD;
   has an inactive fadA gene or chromosomal deletion of all or part of the fadA gene such that the host cell does not express active FadA; and
   has an inactive poxB gene or chromosomal deletion of all or part of the poxB gene such that the host cell does not express PoxB.

16. The genetically modified host cell of claim 1, wherein the FadM has at least 80% amino acid sequence identity to SEQ ID NO:1.

17. The genetically modified host cell of claim 1, wherein the FadM has at least 90% amino acid sequence identity to SEQ ID NO:1.

* * * * *

SEQUENCE LISTING

<160> NUMBER OF SEQ ID NOS: 42

<210> SEQ ID NO 1
<211> LENGTH: 132
<212> TYPE: PRT
<213> ORGANISM: Escherichia coli
<220> FEATURE:
<223> OTHER INFORMATION: Escherichia colii strain DH1 FadM thioesterase,
      thioesterase superfamily protein

<400> SEQUENCE: 1

```
Met Gln Thr Gln Ile Lys Val Arg Gly Tyr His Leu Asp Val Tyr Gln
 1               5                  10                  15

His Val Asn Asn Ala Arg Tyr Leu Glu Phe Leu Glu Glu Ala Arg Trp
                20                  25                  30

Asp Gly Leu Glu Asn Ser Asp Ser Phe Gln Trp Met Thr Ala His Asn
            35                  40                  45

Ile Ala Phe Val Val Asn Ile Asn Tyr Arg Arg Pro Ala
        50                  55                  60

Val Leu Ser Asp Leu Leu Thr Ile Thr Ser Gln Leu Gln Gln Leu Asn
65                  70                  75                  80

Gly Lys Ser Gly Ile Leu Ser Gln Val Ile Thr Leu Glu Pro Glu Gly
                85                  90                  95

Gln Val Val Ala Asp Ala Leu Ile Thr Phe Val Cys Ile Asp Leu Lys
            100                 105                 110

Thr Gln Lys Ala Leu Ala Leu Glu Gly Glu Leu Arg Glu Lys Leu Glu
        115                 120                 125

Gln Met Val Lys
        130
```

<210> SEQ ID NO 2
<211> LENGTH: 707
<212> TYPE: PRT
<213> ORGANISM: Micrococcus luteus
<220> FEATURE:
<223> OTHER INFORMATION: Micrococcus luteus strain NCTC 2665 acyl-CoA
      oxidase, acyl-CoA dehydrogenase, locus Mlut_11700

<400> SEQUENCE: 2

```
Met Thr Val His Glu Lys Leu Ala Pro Gln Ser Pro Thr His Ser Thr
 1               5                  10                  15

Glu Val Pro Thr Asp Val Ala Glu Ile Ala Pro Glu Arg Pro Thr Pro
                20                  25                  30

Gly Ser Leu Asp Ala Ala Ala Leu Glu Glu Ala Leu Leu Gly Arg Trp
            35                  40                  45

Ala Ala Glu Arg Arg Glu Ser Arg Glu Leu Ala Lys Asp Pro Ala Leu
        50                  55                  60

Trp Arg Asp Pro Leu Leu Gly Met Asp Glu His Arg Ala Arg Val Leu
65                  70                  75                  80

Arg Gln Leu Gly Val Leu Val Glu Arg Asn Ala Val His Arg Ala Phe
                85                  90                  95

Pro Arg Glu Phe Gly Gly Glu Asp Asn His Gly Gly Asn Ile Ser Ala
            100                 105                 110

Phe Gly Asp Leu Val Leu Ala Asp Pro Ser Leu Gln Ile Lys Ala Gly
        115                 120                 125

Val Gln Trp Gly Leu Phe Ser Ser Ala Ile Leu His Leu Gly Thr Ala
        130                 135                 140
```

```
Glu His His Arg Arg Trp Leu Pro Gly Ala Met Asp Leu Ser Val Pro
145                 150                 155                 160

Gly Ala Phe Ala Met Thr Glu Ile Gly His Gly Ser Asp Val Ala Ser
                165                 170                 175

Ile Ala Thr Thr Ala Thr Tyr Asp Glu Ala Thr Gln Glu Phe Val Ile
            180                 185                 190

His Thr Pro Phe Lys Gly Ala Trp Lys Asp Tyr Leu Gly Asn Ala Ala
        195                 200                 205

Leu His Gly Arg Ala Ala Thr Val Phe Ala Gln Leu Ile Thr Gln Gly
    210                 215                 220

Val Asn His Gly Val His Cys Phe Tyr Val Pro Ile Arg Asp Glu Lys
225                 230                 235                 240

Gly Ala Phe Leu Pro Gly Val Gly Gly Glu Asp Asp Gly Leu Lys Gly
                245                 250                 255

Gly Leu Asn Gly Ile Asp Asn Gly Arg Leu His Phe Thr Gln Val Arg
                260                 265                 270

Ile Pro Arg Thr Asn Leu Leu Asn Arg Tyr Gly Asp Val Ala Glu Asp
            275                 280                 285

Gly Thr Tyr Ser Ser Pro Ile Ala Ser Pro Gly Arg Arg Phe Phe Thr
        290                 295                 300

Met Leu Gly Thr Leu Val Gln Gly Arg Val Ser Leu Ser Leu Ala Ala
305                 310                 315                 320

Thr Thr Ala Ser Phe Leu Gly Leu His Gly Ala Leu Ala Tyr Ala Glu
                325                 330                 335

Gln Arg Arg Gln Phe Asn Ala Ser Asp Pro Gln Arg Glu Glu Val Leu
                340                 345                 350

Leu Asp Tyr Gln Asn His Gln Arg Arg Leu Ile Asp Arg Leu Ala Arg
        355                 360                 365

Ala Tyr Ala Asp Ala Phe Ala Ser Asn Glu Leu Val Val Lys Phe Asp
    370                 375                 380

Asp Val Phe Ser Gly Arg Ser Asp Thr Asp Val Asp Arg Gln Glu Leu
385                 390                 395                 400

Glu Thr Leu Ala Ala Ala Val Lys Pro Leu Thr Thr Trp His Ala Leu
                405                 410                 415

Asp Thr Leu Gln Glu Ala Arg Glu Ala Cys Gly Gly Ala Gly Phe Leu
        420                 425                 430

Ala Glu Asn Arg Val Thr Gln Met Arg Ala Asp Leu Asp Val Tyr Val
    435                 440                 445

Thr Phe Glu Gly Asp Asn Thr Val Leu Leu Gln Leu Val Gly Lys Arg
450                 455                 460

Leu Leu Thr Asp Tyr Ser Lys Glu Phe Gly Arg Leu Asn Val Gly Ala
465                 470                 475                 480

Val Ser Arg Tyr Val Val His Gln Ala Ser Asp Ala Ile His Arg Ala
                485                 490                 495

Gly Leu His Lys Ala Val Gln Ser Val Ala Asp Gly Gly Ser Glu Arg
        500                 505                 510

Arg Ser Ala Asn Trp Phe Lys Asp Pro Ala Val Gln His Glu Leu Leu
    515                 520                 525

Thr Glu Arg Val Arg Ala Lys Thr Ala Asp Val Ala Gly Thr Leu Ser
530                 535                 540

Gly Ala Arg Gly Lys Gly Gln Ala Ala Gln Ala Glu Ala Phe Asn Thr
545                 550                 555                 560

Arg Gln His Glu Leu Ile Glu Ala Ala Arg Asn His Gly Glu Leu Leu
```

```
                 565                 570                 575

Gln Trp Glu Ala Phe Thr Arg Ala Leu Glu Gly Ile Thr Asp Glu Thr
                 580                 585                 590

Thr Lys Thr Val Leu Thr Trp Leu Arg Asp Leu Phe Ala Leu Arg Leu
             595                 600                 605

Ile Glu Asp Asp Leu Gly Trp Phe Val Ala His Gly Arg Val Ser Ser
        610                 615                 620

Gln Arg Ala Arg Ala Leu Arg Gly Tyr Val Asn Arg Leu Ala Glu Arg
625                 630                 635                 640

Leu Arg Pro Phe Ala Leu Glu Leu Val Glu Ala Phe Gly Leu Glu Pro
                 645                 650                 655

Glu His Leu Arg Met Ala Val Ala Thr Asp Ala Glu Thr Gln Arg Gln
             660                 665                 670

Glu Glu Ala His Ala Trp Phe Thr Ala Arg Arg Ala Ala Gly Glu Glu
        675                 680                 685

Pro Glu Asp Glu Lys Ala Val Arg Ala Arg Glu Lys Ala Ala Arg Gly
690                 695                 700

Arg Arg Gly
705

<210> SEQ ID NO 3
<211> LENGTH: 729
<212> TYPE: PRT
<213> ORGANISM: Escherichia coli
<220> FEATURE:
<223> OTHER INFORMATION: Escherichia coli strain DH1 FadB, fatty
      oxidation complex alpha subunit FadB, enoyl-CoA
      hydratase/isomerase, 3-hydroxyacyl-CoA dehydrogenase,
      multifunctional fatty acid oxidation complex subunit alpha

<400> SEQUENCE: 3

Met Leu Tyr Lys Gly Asp Thr Leu Tyr Leu Asp Trp Leu Glu Asp Gly
1               5                   10                  15

Ile Ala Glu Leu Val Phe Asp Ala Pro Gly Ser Val Asn Lys Leu Asp
            20                  25                  30

Thr Ala Thr Val Ala Ser Leu Gly Glu Ala Ile Gly Val Leu Glu Gln
        35                  40                  45

Gln Ser Asp Leu Lys Gly Leu Leu Arg Ser Asn Lys Ala Ala Phe
    50                  55                  60

Ile Val Gly Ala Asp Ile Thr Glu Phe Leu Ser Leu Phe Leu Val Pro
65                  70                  75                  80

Glu Glu Gln Leu Ser Gln Trp Leu His Phe Ala Asn Ser Val Phe Asn
                85                  90                  95

Arg Leu Glu Asp Leu Pro Val Pro Thr Ile Ala Ala Val Asn Gly Tyr
            100                 105                 110

Ala Leu Gly Gly Gly Cys Glu Cys Val Leu Ala Thr Asp Tyr Arg Leu
        115                 120                 125

Ala Thr Pro Asp Leu Arg Ile Gly Leu Pro Glu Thr Lys Leu Gly Ile
    130                 135                 140

Met Pro Gly Phe Gly Gly Ser Val Arg Met Pro Arg Met Leu Gly Ala
145                 150                 155                 160

Asp Ser Ala Leu Glu Ile Ile Ala Ala Gly Lys Asp Val Gly Ala Asp
                165                 170                 175

Gln Ala Leu Lys Ile Gly Leu Val Asp Gly Val Val Lys Ala Glu Lys
            180                 185                 190

Leu Val Glu Gly Ala Lys Ala Val Leu Arg Gln Ala Ile Asn Gly Asp
```

-continued

```
            195                 200                 205
Leu Asp Trp Lys Ala Lys Arg Gln Pro Lys Leu Glu Pro Leu Lys Leu
210                 215                 220

Ser Lys Ile Glu Ala Thr Met Ser Phe Thr Ile Ala Lys Gly Met Val
225                 230                 235                 240

Ala Gln Thr Ala Gly Lys His Tyr Pro Ala Pro Ile Thr Ala Val Lys
                245                 250                 255

Thr Ile Glu Ala Ala Arg Phe Gly Arg Glu Glu Ala Leu Asn Leu
                260                 265                 270

Glu Asn Lys Ser Phe Val Pro Leu Ala His Thr Asn Glu Ala Arg Ala
            275                 280                 285

Leu Val Gly Ile Phe Leu Asn Asp Gln Tyr Val Lys Gly Lys Ala Lys
        290                 295                 300

Lys Leu Thr Lys Asp Val Glu Thr Pro Lys Gln Ala Ala Val Leu Gly
305                 310                 315                 320

Ala Gly Ile Met Gly Gly Gly Ile Ala Tyr Gln Ser Ala Trp Lys Gly
                325                 330                 335

Val Pro Val Val Met Lys Asp Ile Asn Asp Lys Ser Leu Thr Leu Gly
                340                 345                 350

Met Thr Glu Ala Ala Lys Leu Leu Asn Lys Gln Leu Glu Arg Gly Lys
            355                 360                 365

Ile Asp Gly Leu Lys Leu Ala Gly Val Ile Ser Thr Ile His Pro Thr
370                 375                 380

Leu Asp Tyr Ala Gly Phe Asp Arg Val Asp Ile Val Val Glu Ala Val
385                 390                 395                 400

Val Glu Asn Pro Lys Val Lys Lys Ala Val Leu Ala Glu Thr Glu Gln
                405                 410                 415

Lys Val Arg Gln Asp Thr Val Leu Ala Ser Asn Thr Ser Thr Ile Pro
                420                 425                 430

Ile Ser Glu Leu Ala Asn Ala Leu Glu Arg Pro Glu Asn Phe Cys Gly
            435                 440                 445

Met His Phe Phe Asn Pro Val His Arg Met Pro Leu Val Glu Ile Ile
        450                 455                 460

Arg Gly Glu Lys Ser Ser Asp Glu Thr Ile Ala Lys Val Val Ala Trp
465                 470                 475                 480

Ala Ser Lys Met Gly Lys Thr Pro Ile Val Val Asn Asp Cys Pro Gly
                485                 490                 495

Phe Phe Val Asn Arg Val Leu Phe Pro Tyr Phe Ala Gly Phe Ser Gln
                500                 505                 510

Leu Leu Arg Asp Gly Ala Asp Phe Arg Lys Ile Asp Lys Val Met Glu
            515                 520                 525

Lys Gln Phe Gly Trp Pro Met Gly Pro Ala Tyr Leu Leu Asp Val Val
        530                 535                 540

Gly Ile Asp Thr Ala His His Ala Gln Ala Val Met Ala Ala Gly Phe
545                 550                 555                 560

Pro Gln Arg Met Gln Lys Asp Tyr Arg Asp Ala Ile Asp Ala Leu Phe
                565                 570                 575

Asp Ala Asn Arg Phe Gly Gln Lys Asn Gly Leu Gly Phe Trp Arg Tyr
                580                 585                 590

Lys Glu Asp Ser Lys Gly Lys Pro Lys Lys Glu Glu Asp Ala Ala Val
            595                 600                 605

Glu Asp Leu Leu Ala Glu Val Ser Gln Pro Lys Arg Asp Phe Ser Glu
        610                 615                 620
```

```
Glu Glu Ile Ile Ala Arg Met Met Ile Pro Met Val Asn Glu Val Val
625                 630                 635                 640

Arg Cys Leu Glu Glu Gly Ile Ile Ala Thr Pro Ala Glu Ala Asp Met
            645                 650                 655

Ala Leu Val Tyr Gly Leu Gly Phe Pro Pro Phe His Gly Gly Ala Phe
        660                 665                 670

Arg Trp Leu Asp Thr Leu Gly Ser Ala Lys Tyr Leu Asp Met Ala Gln
            675                 680                 685

Gln Tyr Gln His Leu Gly Pro Leu Tyr Glu Val Pro Glu Gly Leu Arg
        690                 695                 700

Asn Lys Ala Arg His Asn Glu Pro Tyr Tyr Pro Pro Val Glu Pro Ala
705                 710                 715                 720

Arg Pro Val Gly Asp Leu Lys Thr Ala
                725

<210> SEQ ID NO 4
<211> LENGTH: 68
<212> TYPE: DNA
<213> ORGANISM: Artificial Sequence
<220> FEATURE:
<223> OTHER INFORMATION: synthetic quantitative PCR (qPCR) target
      gene-specific amplification primer DH1_fadB_SLIC_F1

<400> SEQUENCE: 4
gcgaagcagt tgcagccttt agtaaatcat gactcataag agctcggtac gaccagatca      60
ccttgcgg                                                               68

<210> SEQ ID NO 5
<211> LENGTH: 60
<212> TYPE: DNA
<213> ORGANISM: Artificial Sequence
<220> FEATURE:
<223> OTHER INFORMATION: synthetic quantitative PCR (qPCR) target
      gene-specific amplification primer DH1_fadB_SLIC_R1

<400> SEQUENCE: 5
tggacggtca tgacgatgct cctgttcgtg agtgggggcg ttcgaacggc ccatcggggt      60

<210> SEQ ID NO 6
<211> LENGTH: 32
<212> TYPE: DNA
<213> ORGANISM: Artificial Sequence
<220> FEATURE:
<223> OTHER INFORMATION: synthetic quantitative PCR (qPCR) target
      gene-specific amplification primer DH1_fadB_F1

<400> SEQUENCE: 6
ctgccatatg ctttacaaag gcgacaccct gt                                    32

<210> SEQ ID NO 7
<211> LENGTH: 28
<212> TYPE: DNA
<213> ORGANISM: Artificial Sequence
<220> FEATURE:
<223> OTHER INFORMATION: synthetic quantitative PCR (qPCR) target
      gene-specific amplification primer DH1_fadB_R1

<400> SEQUENCE: 7
tacagaattc gaacggccca tcggggtg                                         28

<210> SEQ ID NO 8
<211> LENGTH: 35
```

```
<212> TYPE: DNA
<213> ORGANISM: Artificial Sequence
<220> FEATURE:
<223> OTHER INFORMATION: synthetic quantitative PCR (qPCR) target
      gene-specific amplification primer DH1_fadM_F1

<400> SEQUENCE: 8
cgctgaattc acaacgtaag gttattgcgc tatgc                              35

<210> SEQ ID NO 9
<211> LENGTH: 34
<212> TYPE: DNA
<213> ORGANISM: Artificial Sequence
<220> FEATURE:
<223> OTHER INFORMATION: synthetic quantitative PCR (qPCR) target
      gene-specific amplification primer DH1_fadM_R1

<400> SEQUENCE: 9
atgttctaga cttgagcatc cggcaccaca aaac                               34

<210> SEQ ID NO 10
<211> LENGTH: 32
<212> TYPE: DNA
<213> ORGANISM: Artificial Sequence
<220> FEATURE:
<223> OTHER INFORMATION: synthetic quantitative PCR (qPCR) target
      gene-specific amplification primer DH1_hcaT_F1

<400> SEQUENCE: 10
tactgaattc cctgacggga gggactcatg gt                                 32

<210> SEQ ID NO 11
<211> LENGTH: 33
<212> TYPE: DNA
<213> ORGANISM: Artificial Sequence
<220> FEATURE:
<223> OTHER INFORMATION: synthetic quantitative PCR (qPCR) target
      gene-specific amplification primer DH1_hcaT_R1

<400> SEQUENCE: 11
gctatctaga ggagcagatc cgcaaaatgc tcg                                33

<210> SEQ ID NO 12
<211> LENGTH: 74
<212> TYPE: DNA
<213> ORGANISM: Artificial Sequence
<220> FEATURE:
<223> OTHER INFORMATION: synthetic quantitative PCR (qPCR) target
      gene-specific amplification primer L-mbp_SLIC_F1

<400> SEQUENCE: 12
tgtggaattg tgagcggata acaattgcac caacaaggac catagcatat gaaaatcgaa   60
gaaggtaaac tggt                                                     74

<210> SEQ ID NO 13
<211> LENGTH: 57
<212> TYPE: DNA
<213> ORGANISM: Artificial Sequence
<220> FEATURE:
<223> OTHER INFORMATION: synthetic quantitative PCR (qPCR) target
      gene-specific amplification primer L-mbp_SLIC_R1

<400> SEQUENCE: 13
aaggcgcttg ccaggctcgt cgttgccatc ccgaggttgt tgttattgtt attgttg      57

<210> SEQ ID NO 14
```

```
<211> LENGTH: 32
<212> TYPE: DNA
<213> ORGANISM: Artificial Sequence
<220> FEATURE:
<223> OTHER INFORMATION: synthetic quantitative PCR (qPCR) target
      gene-specific amplification primer DH1_paaI_F1

<400> SEQUENCE: 14
agtggaattc gggcgcttct ggagagcggt ta                                 32

<210> SEQ ID NO 15
<211> LENGTH: 33
<212> TYPE: DNA
<213> ORGANISM: Artificial Sequence
<220> FEATURE:
<223> OTHER INFORMATION: synthetic quantitative PCR (qPCR) target
      gene-specific amplification primer DH1_paaI_R1

<400> SEQUENCE: 15
ttattctaga ggcttcacgc atcaggcttc tcc                                33

<210> SEQ ID NO 16
<211> LENGTH: 50
<212> TYPE: DNA
<213> ORGANISM: Artificial Sequence
<220> FEATURE:
<223> OTHER INFORMATION: synthetic quantitative PCR (qPCR) target
      gene-specific amplification primer Ptrc_SLIC_F1

<400> SEQUENCE: 16
gttttgtggt gccggatgct caagtctaga tatcatcgac tgcacggtgc              50

<210> SEQ ID NO 17
<211> LENGTH: 50
<212> TYPE: DNA
<213> ORGANISM: Artificial Sequence
<220> FEATURE:
<223> OTHER INFORMATION: synthetic quantitative PCR (qPCR) target
      gene-specific amplification primer Ptrc_SLIC_R1

<400> SEQUENCE: 17
ttccatgttt cctcctgcgc agggaattcc atggtctgtt cctgtgtga               50

<210> SEQ ID NO 18
<211> LENGTH: 48
<212> TYPE: DNA
<213> ORGANISM: Artificial Sequence
<220> FEATURE:
<223> OTHER INFORMATION: synthetic quantitative PCR (qPCR) target
      gene-specific amplification primer MKS1_SLIC_F1(MKS2)

<400> SEQUENCE: 18
cgtccagcat catctgtaat ctagacctgc gcaggaggaa acatggaa                48

<210> SEQ ID NO 19
<211> LENGTH: 52
<212> TYPE: DNA
<213> ORGANISM: Artificial Sequence
<220> FEATURE:
<223> OTHER INFORMATION: synthetic quantitative PCR (qPCR) target
      gene-specific amplification primer MKS1_SLIC_F2 (fadM)

<400> SEQUENCE: 19
ttttgtggtg ccggatgctc aagtctagac ctgcgcagga ggaaacatgg aa           52

<210> SEQ ID NO 20
<211> LENGTH: 50
```

<212> TYPE: DNA
<213> ORGANISM: Artificial Sequence
<220> FEATURE:
<223> OTHER INFORMATION: synthetic quantitative PCR (qPCR) target
      gene-specific amplification primer MKS1_SLIC_F3 (ptrc)

<400> SEQUENCE: 20
tcacacagga aacagaccat ggaattccct gcgcaggagg aaacatggaa                50

<210> SEQ ID NO 21
<211> LENGTH: 50
<212> TYPE: DNA
<213> ORGANISM: Artificial Sequence
<220> FEATURE:
<223> OTHER INFORMATION: synthetic quantitative PCR (qPCR) target
      gene-specific amplification primer MKS1_SLIC_R1

<400> SEQUENCE: 21
gccaagcttg catgcctgca ggtcgactca tttgtattta ttagcgatgg                50

<210> SEQ ID NO 22
<211> LENGTH: 51
<212> TYPE: DNA
<213> ORGANISM: Artificial Sequence
<220> FEATURE:
<223> OTHER INFORMATION: synthetic quantitative PCR (qPCR) target
      gene-specific amplification primer MKS2_SLIC_F1

<400> SEQUENCE: 22
tcacacagga aacagaccat gggatcccct gcgcaggagg aaacatgtca c              51

<210> SEQ ID NO 23
<211> LENGTH: 48
<212> TYPE: DNA
<213> ORGANISM: Artificial Sequence
<220> FEATURE:
<223> OTHER INFORMATION: synthetic quantitative PCR (qPCR) target
      gene-specific amplification primer MKS2_SLIC_R1

<400> SEQUENCE: 23
ttccatgttt cctcctgcgc aggtctagat tacagatgat gctggacg                  48

<210> SEQ ID NO 24
<211> LENGTH: 23
<212> TYPE: DNA
<213> ORGANISM: Artificial Sequence
<220> FEATURE:
<223> OTHER INFORMATION: synthetic quantitative PCR (qPCR) target
      gene-specific amplification primer Mlut_09310_C123S_F1

<400> SEQUENCE: 24
tctccgccgc gagcgccggc tac                                             23

<210> SEQ ID NO 25
<211> LENGTH: 23
<212> TYPE: DNA
<213> ORGANISM: Artificial Sequence
<220> FEATURE:
<223> OTHER INFORMATION: synthetic quantitative PCR (qPCR) target
      gene-specific amplification primer Mlut_09310_C123S_R1

<400> SEQUENCE: 25
gtagccggcg ctcgcggcgg aga                                             23

<210> SEQ ID NO 26
<211> LENGTH: 30
<212> TYPE: DNA

<210> SEQ ID NO 26
<211> LENGTH: 30
<212> TYPE: DNA
<213> ORGANISM: Artificial Sequence
<220> FEATURE:
<223> OTHER INFORMATION: synthetic quantitative PCR (qPCR) target gene-specific amplification primer Mlut_09310_H275A_F1

<400> SEQUENCE: 26
ccgcgttcat cccggcccag gccaacatgc                              30

<210> SEQ ID NO 27
<211> LENGTH: 30
<212> TYPE: DNA
<213> ORGANISM: Artificial Sequence
<220> FEATURE:
<223> OTHER INFORMATION: synthetic quantitative PCR (qPCR) target gene-specific amplification primer Mlut_09310_H275A_R1

<400> SEQUENCE: 27
gcatgttggc ctgggccggg atgaacgcgg                              30

<210> SEQ ID NO 28
<211> LENGTH: 26
<212> TYPE: DNA
<213> ORGANISM: Artificial Sequence
<220> FEATURE:
<223> OTHER INFORMATION: synthetic quantitative PCR (qPCR) target gene-specific amplification primer Mlut_09310_N306A_F1

<400> SEQUENCE: 28
gcggacgccg gcgccacgtc ggccgc                                  26

<210> SEQ ID NO 29
<211> LENGTH: 26
<212> TYPE: DNA
<213> ORGANISM: Artificial Sequence
<220> FEATURE:
<223> OTHER INFORMATION: synthetic quantitative PCR (qPCR) target gene-specific amplification primer Mlut_09310_N306A_R1

<400> SEQUENCE: 29
gcggccgacg tggcgccggc gtccgc                                  26

<210> SEQ ID NO 30
<211> LENGTH: 61
<212> TYPE: DNA
<213> ORGANISM: Artificial Sequence
<220> FEATURE:
<223> OTHER INFORMATION: synthetic quantitative PCR (qPCR) target gene-specific amplification primer Mlut_11700_SLIC F1

<400> SEQUENCE: 30
gtcattgtcg atgcaattcg caccccgatg ggccgttcga acgccccac tcacgaacag     60 g                                                            61

<210> SEQ ID NO 31
<211> LENGTH: 59
<212> TYPE: DNA
<213> ORGANISM: Artificial Sequence
<220> FEATURE:
<223> OTHER INFORMATION: synthetic quantitative PCR (qPCR) target gene-specific amplification primer Mlut_11700_SLIC R1

<400> SEQUENCE: 31
tgcctctagc acgcgtctca ctatagggcg aattggagct ccaccgcgag gtgacgggg     59

<210> SEQ ID NO 32
<211> LENGTH: 30

```
<212> TYPE: DNA
<213> ORGANISM: Artificial Sequence
<220> FEATURE:
<223> OTHER INFORMATION: synthetic quantitative PCR (qPCR) target
      gene-specific amplification primer Mlut_11700_F2

<400> SEQUENCE: 32
gattcatatg accgtccacg agaagctcgc                                      30

<210> SEQ ID NO 33
<211> LENGTH: 28
<212> TYPE: DNA
<213> ORGANISM: Artificial Sequence
<220> FEATURE:
<223> OTHER INFORMATION: synthetic quantitative PCR (qPCR) target
      gene-specific amplification primer Mlut_11700_R2

<400> SEQUENCE: 33
gattgaattc accgcgaggt gacggggg                                        28

<210> SEQ ID NO 34
<211> LENGTH: 57
<212> TYPE: DNA
<213> ORGANISM: Artificial Sequence
<220> FEATURE:
<223> OTHER INFORMATION: synthetic quantitative PCR (qPCR) target
      gene-specific amplification primer UcfatB1_SLIC_F1

<400> SEQUENCE: 34
caacaataac aataacaaca acctcgggat ggcaacgacg agcctggcaa gcgcctt        57

<210> SEQ ID NO 35
<211> LENGTH: 54
<212> TYPE: DNA
<213> ORGANISM: Artificial Sequence
<220> FEATURE:
<223> OTHER INFORMATION: synthetic quantitative PCR (qPCR) target
      gene-specific amplification primer UcfatB1_SLIC_R1

<400> SEQUENCE: 35
atccgcaagg tgatctggtc gtacgagctc tcacacacgc ggttcagccg gaat           54

<210> SEQ ID NO 36
<211> LENGTH: 20
<212> TYPE: DNA
<213> ORGANISM: Artificial Sequence
<220> FEATURE:
<223> OTHER INFORMATION: synthetic real-time PCR (RT-PCR) primer
      fadM_qPCR_F1

<400> SEQUENCE: 36
ccgctacctt gaatttctcg                                                 20

<210> SEQ ID NO 37
<211> LENGTH: 20
<212> TYPE: DNA
<213> ORGANISM: Artificial Sequence
<220> FEATURE:
<223> OTHER INFORMATION: synthetic real-time PCR (RT-PCR) primer
      fadM_qPCR_ R1

<400> SEQUENCE: 37
acgacgaagg cgatgttatg                                                 20

<210> SEQ ID NO 38
<211> LENGTH: 20
<212> TYPE: DNA
```

<213> ORGANISM: Artificial Sequence
<220> FEATURE:
<223> OTHER INFORMATION: synthetic real-time PCR (RT-PCR) primer hcaT_qPCR_ F1

<400> SEQUENCE: 38
gctgatgctg gtgatgattg                                        20

<210> SEQ ID NO 39
<211> LENGTH: 20
<212> TYPE: DNA
<213> ORGANISM: Artificial Sequence
<220> FEATURE:
<223> OTHER INFORMATION: synthetic real-time PCR (RT-PCR) primer hcaT_qPCR_ R1

<400> SEQUENCE: 39
agtcgcactt tgccgtaatc                                        20

<210> SEQ ID NO 40
<211> LENGTH: 827
<212> TYPE: DNA
<213> ORGANISM: Artificial Sequence
<220> FEATURE:
<223> OTHER INFORMATION: synthetic wild tomato Solanum habrochaites
    (Lycopersicon hirsutum forma glabratum) methyl ketone synthase 1
    (MKS1, ShMKS1), esterase, decarboxylase codon-optimized for
    expression in E. coli

<400> SEQUENCE: 40
ggatcccctg cgcaggagga aacatggaaa aatcaatgtc ccgttcgtc aaaaaacact     60 tcgttctggt tcataccgcc tttcatggtg cttggtgctg gtacaaaatc gtggcactga    120
tgcgtagctc tggccataac gttaccgccc tggatctggg cgcatcaggt attaacccga    180
aacaggcgct gcaaatcccg aattttcag actatctgtc gccgctgatg gaatttatgg     240
cctcactgcc ggcaaatgaa aaaattatcc tggtgggtca cgcactgggc ggtctggcta    300
tttcgaaagc gatggaaacc tttccggaaa aaatcagcgt cgctgtgttc ctgtctggcc    360
tgatgccggg tccgaacatt gatgccacca cggtttgcac gaaagctggc agcgcagtcc    420
tgggtcagct ggacaattgt gtgacctatg aaaacggccc gacgaatccg ccgaccacgc    480
tgattgccgg tccgaaattt ctggcaacca cgtctacca tctgtctccg atcgaagatc     540
tggcactggc aacggcactg gttcgtccgc tgtatctgta cctggcggaa gacattagta    600 agaagtggt tctgagttcc aaacgttacg gctccgttaa acgcgtcttt atcgtggcta     660
ccgaaaacga tgcgctgaaa aaagaatttc tgaaactgat gatcgagaaa acccgccgg    720 atgaagttaa agaaatcgaa ggttccgacc acgtcaccat gatgtcaaaa ccgcaacaac    780
tgttcacgac cctgctgtcc atcgctaata aatacaaatg atctaga               827

<210> SEQ ID NO 41
<211> LENGTH: 656
<212> TYPE: DNA
<213> ORGANISM: Artificial Sequence
<220> FEATURE:
<223> OTHER INFORMATION: synthetic wild tomato Solanum habrochaites
    (Lycopersicon hirsutum forma glabratum) methyl ketone synthase II
    (chloroplast) (MKS2, ShMKS2), beta-ketoacyl-ACP thioesterase
    codon-optimized for expression in E. coli

<400> SEQUENCE: 41
ggatcccctg cgcaggagga aacatgtcac actctttctc aatcgcaacc aacatcctgc     60
tgctgaatca tggctcgccg ccgtcaacct tcccggtcat cccgcatcgc cagctgccgc    120

```
tgccgaacct gcgtctgagc agccgtaaaa gtcgctcctt tgaagcacat agtgctttcg    180
atctgaaatc aacccagcgc atgtcggatc aagtgtatca tcacgacgtg gaactgacgg    240
ttcgtgatta cgaactggac cagtttggcg tggttaacaa tgcgacctat gcctcatact    300
gccaacattg tcgccacgca ttcctggaaa aaattggcgt ttcggtcgat gaagtcaccc    360
gtaacggtga cgcactggca gtgacggaac tgagtctgaa atttctggcg ccgctgcgct    420
ccggcgatcg ttttgtcgtg cgtgcgcgcc tgtctcattt cacggttgcc cgcctgtttt    480
tcgaacactt tatcttcaaa ctgccggacc aagaaccgat tctggaagca cgtggtatcg    540
ctgtctggct gaatcgtagc tatcgcccga ttcgtatccc gtctgaattt aatagtaaat    600
tcgtcaaatt cctgcaccaa aaagttgtg gcgtccagca tcatctgtaa tctaga         656
```

<210> SEQ ID NO 42
<211> LENGTH: 1161
<212> TYPE: DNA
<213> ORGANISM: Artificial Sequence
<220> FEATURE:
<223> OTHER INFORMATION: synthetic California bay laurel Umbellularia californica lauroyl-acyl carrier protein thioesterase (UcFatB1), 12:0-acyl carrier protein thioesterase, acyl-[acyl-carrier-protein] hydrolase codon-optimized for expression in E. coli

<400> SEQUENCE: 42

```
gaattcatgg caacgacgag cctggcaagc gccttctgtt cgatgaaagc tgttatgctg     60
gcccgtgatg gccgtggtat gaaaccgcgt agctcagatc tgcagctgcg tgcaggcaac    120
gctccgacct cgctgaaaat gatcaacggt accaaattca gttacacgga atccctgaaa    180
cgcctgccgg attggagtat gctgtttgcc gtcattacca cgatcttctc cgcggccgaa    240
aaacagtgga ccaacctgga atggaaaccg aaaccgaaac tgccgcaact gctggatgac    300
cattttggtc tgcacggcct ggttttttcgt cgcacccttcg cgattcgtag ctatgaagtc    360
ggcccggatc gctcaacctc gatcctggcc gtgatgaacc atatgcagga agcgacgctg    420
aatcacgcca aaagcgtggg tattctgggc gatggtttcg gcaccacgct ggaaatgtct    480
aaacgtgacc tgatgtgggt ggttcgtcgc acccatgtcg cagtggaacg ctacccgacc    540
tggggcgata cggttgaagt cgaatgctgg atcggtgctt ctggcaacaa tggtatgcgt    600
cgcgatttcc tggttcgtga ctgcaaaacc ggtgaaattc tgacccgctg tacgagcctg    660
tctgtgctga tgaataccog tacgcgtcgc ctgagtacga tcccggatga agttcgcggc    720
gaaattggtc cggcatttat cgacaacgtg gctgttaaag atgacgaaat caaaaaactg    780
cagaaactga cgatagcac cgcagactat atccaaggcg gtctgacgcc gcgttggaac    840
gatctggacg ttaatcagca tgtgaacaat ctgaaatacg tcgcgtgggt gtttgaaacc    900
gtgccggatt caattttcga atcgcatcac atcagctctt ttaccctgga ataccgtcgc    960
gaatgcacgc gtgatagcgt gctgcgctct ctgaccaccg ttagtggcgg tagttccgaa   1020
gcgggcctgg tttgtgacca cctgctgcaa ctggaaggcg gttccgaagt cctgcgtgcc   1080
cgcaccgaat ggcgcccgaa actgaccgat tccttccgtg gcattagtgt gattccggct   1140
gaaccgcgtg tgtgagagct c                                              1161
```